(12) United States Patent
Dorshow et al.

(10) Patent No.: US 10,137,207 B2
(45) Date of Patent: *Nov. 27, 2018

(54) METHODS OF USING OPTICAL AGENTS

(71) Applicant: MediBeacon Inc., St. Louis, MO (US)

(72) Inventors: Richard B. Dorshow, St. Louis, MO (US); Raghavan Rajagopalan, Solon, OH (US); Dennis A. Moore, St. Louis, MO (US); Scott T. Depierro, Madison, CT (US)

(73) Assignee: MediBeacon, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/919,967

(22) Filed: Oct. 22, 2015

(65) Prior Publication Data
US 2016/0045619 A1    Feb. 18, 2016

Related U.S. Application Data

(63) Continuation of application No. 11/995,270, filed as application No. PCT/US2006/039732 on Oct. 11, 2006, now Pat. No. 9,283,288.
(Continued)

(51) Int. Cl.
*A61B 5/00* (2006.01)
*A61K 49/00* (2006.01)
(Continued)

(52) U.S. Cl.
CPC ........ *A61K 49/0021* (2013.01); *A61B 5/0071* (2013.01); *A61B 5/0077* (2013.01);
(Continued)

(58) Field of Classification Search
CPC .. A61B 2017/00022; A61B 2019/5231; A61B 5/0059; A61B 5/0071; A61B 5/418;
(Continued)

(56) References Cited

U.S. PATENT DOCUMENTS 3,733,397 A * 5/1973 Erikson et al. .... A61K 49/0442
424/9.453
5,423,321 A   6/1995 Fontenot
(Continued)

FOREIGN PATENT DOCUMENTS

WO    2006071759 A2    7/2006
WO    2006115633 A2    11/2006

OTHER PUBLICATIONS

Sohtell M et al: "Fitc-inulin as a kidney tubule marker in the rat", Acta Physiologica Scandinavica, Oxford, GB, vol. 119, 1983, pp. 313-316, XP008067913, Abstract, p. 3214, figure 2, p. 315 lines 6-17.
(Continued)

*Primary Examiner* — Elmer Chao
(74) *Attorney, Agent, or Firm* — Armstrong Teasdale LLP

(57) ABSTRACT

In certain aspects, the invention relates to processes for using renally excretable optical agents to detect one or more tissues of the renal system of a surgical patient. In certain aspects, the invention relates to a kit including a biocompatible composition containing one or more optical agents and instructions for using the optical agent(s) in a process of the present invention.

7 Claims, 7 Drawing Sheets
(3 of 7 Drawing Sheet(s) Filed in Color)

Related U.S. Application Data

(60) Provisional application No. 60/776,782, filed on Feb. 24, 2006.

(51) Int. Cl.
*A61B 5/20* (2006.01)
*A61B 17/00* (2006.01)
*A61B 17/42* (2006.01)

(52) U.S. Cl.
CPC .............. *A61B 5/20* (2013.01); *A61B 5/4836* (2013.01); *A61B 5/0059* (2013.01); *A61B 5/418* (2013.01); *A61B 2017/00022* (2013.01); *A61B 2017/00274* (2013.01); *A61B 2017/00823* (2013.01); *A61B 2017/4216* (2013.01); *A61B 2017/4233* (2013.01); *A61B 2562/0233* (2013.01)

(58) Field of Classification Search
CPC ....... A61B 5/0077; A61B 5/20; A61B 5/4836; A61B 2017/00274; A61B 2017/00823; A61B 2017/4216; A61B 2017/4233; A61B 2562/0233; A61K 49/0021
See application file for complete search history.

(56) References Cited

U.S. PATENT DOCUMENTS

| | | | |
|---|---|---|---|
| 5,517,997 A | 5/1996 | Fontenot | |
| 5,769,791 A * | 6/1998 | Benaron | G01N 21/4795 600/473 |
| 5,879,306 A | 3/1999 | Fontenot et al. | |
| 5,954,652 A | 9/1999 | Heyman | |
| 6,007,814 A | 12/1999 | Scheinberg | |
| 6,228,344 B1 | 5/2001 | Dorshow et al. | |
| 6,280,703 B1 | 8/2001 | Combs et al. | |
| 6,597,941 B2 | 7/2003 | Fontenot et al. | |
| 6,761,878 B2 | 7/2004 | Achilefu et al. | |
| 6,887,854 B2 | 5/2005 | Achilefu et al. | |
| 2003/0232016 A1 | 12/2003 | Heinrich | |
| 2004/0223913 A1* | 11/2004 | Achilefu | A61K 31/403 424/9.6 |
| 2005/0192478 A1 | 9/2005 | Williams et al. | |
| 2006/0239921 A1* | 10/2006 | Mangat | A61K 49/0034 424/9.6 |

OTHER PUBLICATIONS

Hackstein N et al: "Measurement of Single-Kidney Glomerula Filetration Rate Using a Contrast-Enhanced Dynamic Gradient-Echo Sequence and the Rutland-Patlak Plot Technique", J. Magn. Res. Imag., vol. 18, 2003, pp. 714-725, XP007903255, Abstract, p. 715 second column, par. 3-p. 716 first column paragraph 2; p. 720 Figure 3.

JW Utrie, "Bladder and Ureteral Injury: Prevention and Management", Clin. Obstet. Gynecol, 1998, 41(3); pp. 755-763.

N. Zelenko et al., Normal Ureter Size on Unenhanced Helical CT, Am. J. Roentgenol. 2004, 182:1039-1041.

F. Chahin, et al., The Implications of Lighted Ureteral Stenting in Laparoscopic Colectomy, JSLS, 2002, 6:49-52.

Prescribing Information for IC Green—Indocyanine Green for Injection.

De Grand et al., "An Operational Near-Infrared Fluorescence Imaging System Prototype for Large Animal Surgery", Technology in Cancer Research & Treatment, vol. 2, No. 6, Dec. 2003, pp. 553-562.

U.S. Appl. No. 60/815,712.

* cited by examiner

METHODS OF USING OPTICAL AGENTS

This application is a continuation of U.S. patent application Ser. No. 11/995,270 filed Jan. 10, 2008, which is a National Stage Entry of PCT/US06/39732 filed Oct. 11, 2006, which claims priority to U.S. Provisional Patent Application Ser. No. 60/776,782, filed Feb. 24, 2006, which is incorporated herein by reference.

FIELD OF THE INVENTION

In certain embodiments, the invention relates to processes for using optical agents to detect one or more tissues of the renal system of a surgical patient. In certain embodiments, the invention relates to kits including a biocompatible composition and instructions for using the composition to optically detect a tissue of the renal system of a patient.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Abdominal and pelvic surgical procedures carry a risk of accidental injury to the tissues of the renal system, and in particular, to the bladder and/or ureters. The bladder is a hollow, muscular, and elastic vesicle situated in the anterior part of the pelvic cavity. The bladder serves as a reservoir for urine until it can be eliminated from the body through the urethra. The ureters are delicate, small-diameter muscular vessels that carry urine from the kidneys to the bladder. In a healthy individual, the ureters tend to be about 25 cm to about 30 cm long and up to about 3 mm in diameter (J. W. Utrie, Bladder and Ureteral Injury, *Clin. Obstet. Gynecol.*, 1998, 41(3):755-763; N. Zelenko et al., Normal Ureter Size on Unenhanced Helical CT, *Am. J. Roentgenol.* 2004, 182: 1039-1041). In part because of their small diameter, the ureters are often difficult to identify in a surgical field. This is especially true in laparoscopic procedures, because the surgeon generally has a limited view of the surgical field and cannot use tactile perception to aid in identification of organs and tissues. Thus, in such procedures there is often a risk that the bladder may be unintentionally penetrated or that the ureters may be unintentionally nicked, severed, ligated, crushed, or otherwise injured.

Injuries to the bladder and ureter are not uncommon complications of hysterectomy. Hysterectomy is the second most common surgery among women in the United States, with over 600,000 such procedures performed each year (Women's Reproductive Health: Hysterectomy, http://www.cdc.gov/reproductivehealth/WomensRH/Hysterectomy.htm). Ureteral injury occurs in approximately 0.5 to 2 percent of all hysterectomies and routine gynecologic pelvic operations, and in approximately 10 percent of radical hysterectomies (S. B. Brandes, Urologic Complications from Pelvic and Vaginal Surgery: How to Diagnose and Manage, http://www.urology.wustl.edu/PatientCare/UrologicComplications.asp). Laparoscopic hysterectomy has become more popular in recent years due to its advantages over conventional surgical methods (e.g., smaller incisions, reduced hospital stays, and a speedier return to normal activities). However, laparoscopic hysterectomy generally carries a greater risk of accidental injury to the bladder and ureter as compared to conventional surgical procedures. As another example, the incidence of ureteral injury during colorectal surgery has been reported as ranging from 0.2 to 4.5% (F. Chahin, et al., The Implications of Lighted Ureteral Stenting in Laparoscopic Colectomy, *JSLS*, 2002, 6:49-52).

Injury to the urinary tract can result in various complications, some of which may be life-threatening. Such complications include voiding difficulties, incontinence, detrusor instability, bowel obstruction, persistent abdominal and/or flank pain, urinary tract infection, pyelonephritis, loss of kidney function that may require surgical removal of the kidney, fever/body-wide responses to serious infection, and possible death. In particular, ureteral injuries that occur during a surgical procedure are often not immediately recognized and can therefore lead to very serious complications. Such ureteral injuries may result in permanent kidney damage, possibly requiring removal of a kidney, and in some cases are life-threatening.

Methods for detecting or visualizing a ureter during abdominal or pelvic surgery generally have involved inserting a lighted catheter or stent through the urethra and bladder and into the ureter. Such methods are particularly popular in laparoscopic procedures, where tactile identification of the ureters is not possible. For example, U.S. Pat. Nos. 5,423,321, 5,517,997, 5,879,306, and 6,597,941 disclose infrared illuminated ureteral catheters coupled with infrared detection systems. Similarly, U.S. Pat. No. 5,954,652 describes a double lumen ureteral catheter device made of light transmitting material, one lumen of which houses a single fiber optic filament capable of illuminating the catheter with visible light.

Placement of a lighted ureteral catheter or stent is a highly invasive procedure. Some surgeons believe that ureteral catheters do not prevent injuries to the renal system and may in fact predispose patients to such injuries. Furthermore, placement of a lighted ureteral catheter or stent is associated with its own list of complications. For example, in one study of complications associated with placement of a lighted ureteral stent during laparoscopic colectomy, nearly all (98.4%) patients developed gross hematuria lasting approximately three days. Less frequent complications included reflux anuria which in some cases required renal support with hemodialysis for three to six days, and urinary tract infection. Placement of lighted catheters also prolonged anesthetic time by on average 26 minutes, thus increasing the cost of the procedure. Where visualization of both ureters is desired, bilateral placement of ureteral catheters may increase the likelihood and severity of these complications (F. Chahin, et al., The Implications of Lighted Ureteral Stenting in Laparoscopic Colectomy, *JSLS*, 2002, 6:49-52).

Because of the risk of injury to the tissues of the renal system during abdominal and pelvic surgical procedures and because of the complications associated with the placement of lighted ureteral catheters, it would be desirable to develop a non-invasive method by which a surgical patient's bladder and/or ureters can be readily visualized or detected. Furthermore, because ureteral injuries that occur during surgical procedures are often not immediately recognized and can result in very serious complications, a method facilitating immediate detection of ureteral injuries during a surgical procedure would be advantageous.

Although the majority of ureteral injuries occur in patients with no identifiable risk factors, a non-invasive method for visualization or detection of the ureters during a surgical procedure would be particularly desirable for individuals who are at increased risk for ureteral injury. For example, prolapse patients and pregnant women may have extremely dilated and thin ureters and thus are more at risk for ureteral injury. Furthermore, congenital defects in the urinary system, such as ureteral duplication, can alter the anatomy of the renal system and thus increase the likelihood of injury to the bladder and/or ureter during a surgical procedure.

SUMMARY

Certain aspects commensurate in scope with the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Among some of the various aspects of the present invention is the use of one or more optical dyes in a surgical procedure to enable a surgeon or other health care professional to demarcate a tissue of the renal system. Advantageously, the surgeon or other health care professional can thereby avoid, target and/or assess the integrity of the tissue before, during and/or after the surgical procedure.

One aspect of the present invention is directed to a process for using an optical agent in a surgical procedure. In this process, a renally excretable optical agent is administered to a patient to cause the optical agent to appear in the patient's urine. Further, a first tissue of the patient's renal system is irradiated with non-ionizing radiation, and the agent is optically detected in the irradiated first tissue to demarcate the position of the first tissue (e.g., relative to surrounding and/or adjacent tissue).

Another aspect of the invention is directed a process for using an optical agent in a surgical procedure. In this process, a surgical field of a patient is irradiated with non-ionizing radiation while a renally excretable optical agent is located in a first tissue of the patient's renal system in the surgical field. The first tissue is irradiated to detect the optical agent in the first tissue. A second tissue of the patient is then surgically manipulated based, at least in part, on the optical detection of the agent in the first tissue.

Yet another aspect of the invention is directed to a process for using an optical agent in a surgical procedure. In this process, a renally excretable optical agent is delivered to at least one tissue of a renal system of a patient, and the tissue(s) is(are) irradiated with non-ionizing radiation. The optical agent is detected (based, at least in part, on irradiation of the tissue) to determine if the agent is retained within the tissue(s) of the renal system of the patient.

Still another aspect of the invention is directed to a kit. This kit includes a biocompatible composition and instructions for using the composition to optically detect a tissue of the renal system of a patient. The biocompatible composition included in this kit contains at least one renally excretable optical agent.

Various refinements exist of the features noted above in relation to the various aspects of the present invention. Further features may also be incorporated in these various aspects as well. These refinements and additional features may exist individually or in any combination. For instance, various features discussed below in relation to one or more of the described exemplary embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

The patent or application file contains at least one photograph executed in color. Copies of this patent or patent application publication with color photograph(s) will be provided by the Office upon request and payment of the necessary fee.

DETAILED DESCRIPTION OF SPECIFIC EMBODIMENTS

Figure 1:
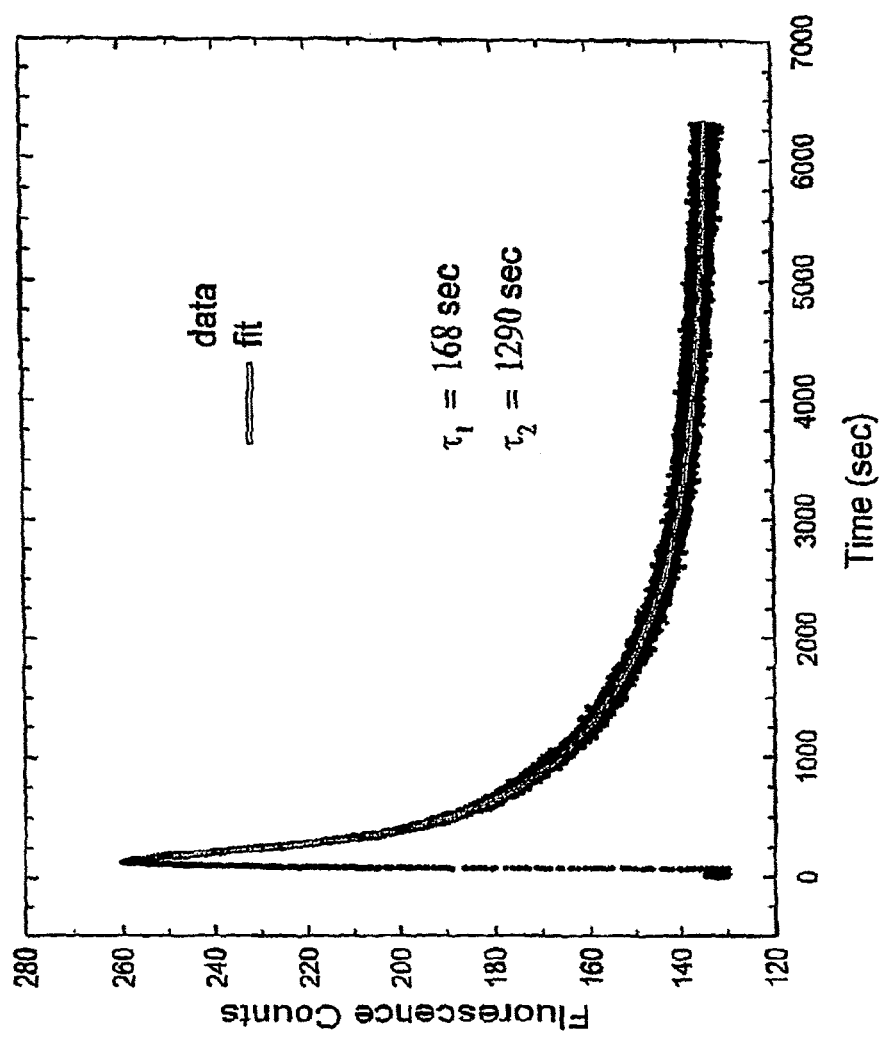
FIG. 1 shows the renal clearance of an optical agent (3,6-diaminopyrazine-2,5-dicarboxylic acid) in an intact rat. Data were generated in accordance with the procedures set forth in Example 1.

In accordance with the present invention, one or more optical agents that are at least partially renally excretable, is/are administered to a surgical patient to cause the optical agent(s) to appear in the patient's urine. Once there, the optical agent(s) may be detected in the patient's renal system by irradiating one or more tissues of the renal system with non-ionizing radiation having a wavelength that enables optically detection of the optical agent(s). The optical agent(s) may thereby be utilized to demarcate a tissue that contains or contained urine for a variety of purposes.

In one embodiment, the appearance of an optical agent in urine of a patient permits a surgeon or other health care professional to readily distinguish between one or more tissues of the renal system (containing the urine) and surrounding tissues. The surgeon can thus avoid accidental injury to the renal system (e.g., nicking or severing of the ureter) during a surgical procedure involving a nearby organ or tissue.

Alternatively, the appearance of an optical agent in the urine of a patient permits a surgeon or other health care professional to identify and/or delimit the target of the surgical procedure. For example, during a nephrectomy or other surgery procedure involving on one or more tissues of the renal system, the surgeon or other health care professional may readily identify the kidney or other renal tissue containing urine by detection of the optical agent.

In yet another alternative approach, the appearance of an optical agent in the urine of a patient permits a surgeon or other health care professional to assess the integrity of one or more tissues of the renal system. For example, if an optical agent remains confined within the renal system upon completion of a surgical procedure, this indicates that the ureter was not nicked during the surgical procedure and that the integrity of the ureter and other tissues of the renal system has not been compromised. In contrast, if the ureter or another tissue of the renal system has been damaged, the surgeon or other health care professional may readily identify the location of such damage (e.g., by observing the egress of dye from the site of the damage).

In general, the surgical patient or patient is a human or other warm-blooded animal that is a candidate for, is undergoing, or has undergone any surgical procedure involving a tissue or organ located in the abdominal or pelvic region and/or wherein the abdominal cavity is at least partially penetrated. In one embodiment, the patient is a human patient. In another embodiment, the patient is a non-human animal undergoing abdominal or pelvic surgery. For example, in non-human animals undergoing oophorectomy (also known as ovariotomy or spaying), the processes of the present invention can be used to avoid accidental injury to the ureter and/or other tissues of the renal system.

I. Surgical Procedures

In general, the optical agent may be used in conjunction with a range of surgical methods. For example, the optical agent may be used in "open" procedures or in minimally invasive surgeries, sometimes referred to as bandaid or keyhole surgeries. In open procedures, an incision sufficiently large to expose the entire operative area is made with a scalpel or other knife. In minimally invasive surgeries, one or more much smaller incisions are typically made, through which a laparoscope and/or other endoscopic tools may be inserted to allow a surgeon to view and/or surgically manipulate a patient's organs and/or tissues.

Surgical procedures in which the processes of the present invention can be used to aid a surgeon include, but are not limited to, for example, total or partial hysterectomy, oophorectomy, tubal ligation, surgical removal of ovarian cysts, anterior repair of the vaginal wall, caesarean section, repair of a pelvic prolapse, pelvic mass resection, removal of a fallopian tube, adnexectomy (removal of a fallopian tube and an ovary), removal of an ectopic pregnancy, vasectomy, prostatectomy, hernia repair surgery, colectomy, cholecystectomy, appendectomy, hepatobiliary surgery (e.g., liver transplant surgery or removal of the gallbladder), splenectomy, distal or total pancreatectomy, the Whipple procedure, removal of inflammatory or malignant tumors in the abdominal or pelvic regions, abdominal or pelvic lymphadenectomy (removal of lymph nodes), and other surgical procedures performed in the abdominal or pelvic regions.

To various degrees, these and other surgical procedures performed in the abdomen or pelvic cavity carry a risk of accidental damage to the tissues of the renal system, and in particular, to the ureter. The risk of damage to the ureter and other tissues of the renal system is especially high in laparoscopic surgical procedures, because the surgeon has a limited view of the surgical area and is unable to use tactile perception to identify these structures. In one embodiment, therefore, one or more optical agents are administered to avoid such accidental damage by permitting a surgeon to distinguish one or more tissues of the renal system from surrounding tissues. For example, the process of the present invention permits a surgeon to distinguish one or more tissues of the renal system from tissues of the male and female reproductive systems, tissues of the digestive tract, the pancreas, the gallbladder, the liver, the bile duct, and/or the spleen. The process of the present invention also permits a surgeon to distinguish one or more tissues of the renal system from nearby arteries, veins, lymphatic vessels, and other tissues.

As previously noted, one aspect of the present invention is the use of one or more optical agents to demarcate at least one tissue of the renal system of a patient during a surgical procedure. For example, the process of the present invention can be used to enable the surgeon or other healthcare individual to avoid the ureter(s), the bladder, and/or the urethra. In a healthy individual, urine flows from the kidneys through the ureter and collects in the bladder, where it is stored until it is eliminated from the body through the urethra. Thus, in the process of the present invention, detection of the optical agent(s) in the ureter and bladder is possible due to the accumulation of the agent(s) in urine present in those structures. Detection of the optical agent(s) in the urethra is possible, for example, where residue of urine containing the optical agents is present on the walls of the urethra, or where a urinary catheter facilitates continuous flow of urine through the urethra.

Alternatively, another aspect of the present invention is the use of one or more optical agents to demarcate the target of a surgical procedure. Such surgical procedures include, but are not limited to, for example, nephrectomy, renal transplantation surgery, resection of a ureteral segment during removal of a tumor, bladder neck suspension surgery, and surgical removal of kidney stones.

A further aspect of the present invention is the use of the optical agent(s) to assess the integrity of the renal system. Such an assessment can be made before, during, and/or after a surgical procedure performed on the renal system and/or other organ and/or tissue in the abdominal and/or pelvic region. Confinement of the optical agent to the tissues of the renal system indicates that no damage to the renal system (e.g., nicking of the ureter) has occurred. If damage or injury to a tissue of the renal system has occurred, the process of the present invention allows a surgeon to rapidly identify the location of such damage or injury (e.g., by observing the egress of dye from the site of damage).

A further aspect of the present invention is the use of the optical agent(s) to detect one or more tissues of the renal system during a diagnostic laparoscopic procedure.

Depending upon the surgical technique employed, the presence of the optical agent in a first tissue may be detected by irradiating the entire surgical field. This approach could be used, for example, in open surgical procedures. Alternatively, only a portion of the surgical field or the specific site(s) to be monitored may be illuminated, for example, using a laparoscope or other endoscopic tool.

In general, any source of irradiation capable of providing non-ionizing radiation of a desired wavelength may be used. For example, in one embodiment, the operating room lighting (e.g., fluorescent or incandescent lighting) emits light of the desired wavelength. In another embodiment, the source of irradiation is a laser. In yet another embodiment, the source of irradiation is a hand-held light. Other sources of irradiation that can be used include, but are not limited to, lighted catheters, endoscopes, fiber optic probes, light emitting diodes (LEDs), lighted headbands (also called headlights), and the like. A surgical instrument that contains or is configured with an illumination system may also be employed. Examples of such instruments include the fiber optic instruments available from BioSpec (Moscow, Russia) and the TC-I fiber optic tool for photodynamic therapy with fine needle tip for irradiating interstitial tumors (http://www.biospecsuf_Fiber_Optics_e.html).

Any of the optical detection methods available in the art can be used in the present invention. Spectroscopic measurements can be separated into three broad categories: absorbance, scattering/reflectance, and emission. Absorbance assays involve relating the amount of incident light that is absorbed by a sample to the type and number of molecules in the sample. For example, in case of absorbance measurement, it is desirable that the wavelength of the non-ionizing radiation that is used is one which is absorbed by the optical agent. Most commonly, absorbance is measured indirectly by studying the portion of incident light that emerges from the sample. Scattering assays are similar to absorbance in that the measurement is based on the amount of incident light that emerges or is transmitted from the sample or tissue. However, in the case of scattering, the signal increases with the number of interactions, whereas, in the case of absorbance, the signal is inversely proportional to the interactions. Emission assays look at electromagnetic emissions from a sample other than the incident light. In each case, the measurements may be broad spectrum or frequency-specific depending on the particular assay. Most commonly, emission assays involve the measurement of luminescence.

Luminescence is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. Luminescence assays involve detection and interpretation of one or more properties of the luminescence or associated luminescence process. These properties include intensity, excitation and/or emission spectrum, polarization, lifetime, and energy transfer, among others. These properties also include time-independent (steady-state) and/or time-dependent (time-resolved) properties of the luminescence. Representative luminescence assays include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and bioluminescence resonance energy transfer (BRET), among others. By way of example, when a fluorescent optical agent is used in the present invention, it is desirable that the wavelength of non-ionizing radiation be such that it excites the optical agent. This excitation causes the molecule to emit part of the absorbed energy at a different wavelength, and the emission can be detected using fluorometric techniques as described above. One skilled in the art can readily determine the most appropriate detection technique based on, in part, the specific optical agent(s) administered, the tissue to be detected, and the type of surgical procedure involved. For example, in some embodiments, the surgeon will be able to see the optical agent in the surgical field. Other embodiments employ an optical agent that can be detected using a laparoscopic instrument.

Upon irradiation with electromagnetic radiation of the proper wavelength, an optical agent may be detected by visual or other optical means. For example, optical detection may be achieved using the unaided eye or by one or more imaging or detecting devices (e.g., a camera, charged coupled device (CCD), photomultiplier tube (PMT), avalanche diode, photodiodes), or detection involving an electronic processing step (e.g., detecting, enhancing, processing, analyzing, quantitating, or otherwise manipulating a signal using software or other means).

II. Dyes/Optical Agents

The optical agents (also referred to as optical dyes) used in the process of the present invention are at least partially renally excretable. That is, upon administration to a patient, at least a fraction of the administered dose of the optical agent will be excreted by way of the renal system. In general, the size and hydrophobicity of a pharmaceutical or diagnostic agent tends to influence the route by which it is excreted when it is administered to a patient. Small, hydrophilic molecules tend to be excreted via the renal system, whereas larger, hydrophobic molecules tend to be excreted via the hepatobiliary route. Thus, in general, the optical agents employed in the process of the present invention are preferably relatively smaller in size and/or relatively more hydrophilic than dyes excreted predominantly via the hepatobiliary route. The optical agents may be coupled or associated with moieties which render them more hydrophilic and thus increase their capacity to be excreted via the renal system. For example, a hydrophilic chelating agent, such as ethylenediaminetetraacetic acid (EDTA), diethylenetriaminepentaacetic acid (DPTA), 1,4,7,10-tetraazacyclododecanetetraacetic acid (DOTA), or their derivatives, can be attached to an optical agent. The degree to which an optical agent is renally excreted can be determined empirically by a process such as that described herein in Examples 1 and 2 or by other processes known to those skilled in the art.

Preferably, the optical agent(s) is/are untargeted. That is, the optical agent(s) is/are not associated with a carrier or conjugate which increases the selectivity of the optical agent for localization in a particular organ or tissue. Rather, any biocompatible optical agent that is excreted via the renal system and that is capable of being detected therein may be used in the process and kit of the present invention.

The renally excretable optical agents of the present invention are generally chromophores or fluorophores, and the like. Optimal absorption or excitation maxima for the optical agents will vary depending on the optical agent employed, but in general, the optical agents of the present invention will absorb or be excited by light in the ultraviolet (UV), visible, or infrared (IR) range of the electromagnetic spectrum. For example, the non-ionizing radiation employed in the process of the present invention may range in wavelength from about 350 nm to about 1200 nm.

Exemplary optical agents include, but are not limited to, the phenylxanthenes, phenothiazines, phenoselenazines, cyanines, indocyanines, squaraines, dipyrrolo pyrimidones, anthraquinones, tetracenes, quinolines, pyrazines, acridines, acridones, phenanthridines, azo dyes, rhodamines, phenoxazines, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Specific optical agents that may be used in the process include, but are not limited to, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine (NIRD)-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl) amino]pyrazine, 3,6-[(N,N,N',N'-tetrakis(2-hydroxyethyl) amino]pyrazine-2,5-dicarboxylic acid, 3,6-bis(N-azatedino) pyrazine-2,5-dicarboxylic acid, 3,6-bis(N-morpholino) pyrazine-2,5-dicarboxylic acid, 3,6-bis(N-piperazino) pyrazine-2,5-dicarboxylic acid, 3,6-bis(N-thiomorpholino) pyrazine-2,5-dicarboxylic acid, 3,6-bis(N-thiomorpholino) pyrazine-2,5-dicarboxylic acid S-oxide, 2,5-dicyano-3,6-bis (N-thiomorpholino)pyrazine S,S-dioxide, indocarbocyaninetetrasulfonate, chloro indocarbocyanine, and 3,6-diaminopyrazine-2,5-dicarboxylic acid (see Examples 1-2 herein), and 3,6-diaminopyrazine-2,5-dicarboxylic acid (see Example 3 herein).

In one exemplary embodiment, the optical agent is excited by light having a wavelength in the blue range of the visible portion of the electromagnetic spectrum (from about 430 nm to about 500 nm) and emits at a wavelength in the green range of the visible portion of the electromagnetic spectrum (from about 520 nm to about 565 nm). For example, fluorescein dyes can be excited with light with a wavelength of about 488 nm and have an emission wavelength of about 520 nm. As another example, 3,6-diaminopyrazine-2,5-dicarboxylic acid can be excited with light having a wavelength of about 470 nm and fluoresces at a wavelength of about 532 nm (see Example 3 and FIG. 4 herein).

In another embodiment, the excitation and emission wavelengths of the optical agent may fall in the near-infrared range of the electromagnetic spectrum. For example, indocyanine dyes, such as indocyanine green, can be excited with light with a wavelength of about 780 nm and have an emission wavelength of about 830 nm.

By way of example, optical agents that may be employed in the processes of the present invention include, but are not limited to, those represented by Formulas 1 to 8 below. The optical agents of Formulas 1-6 are hydrophilic and absorb light in the visible and near infrared regions of the electromagnetic spectrum.

In one group of embodiments, compounds for use as optical agents in the processes of the present invention correspond to Formula 1:

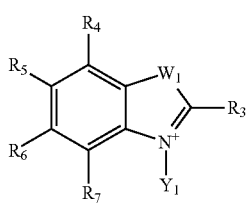

Formula 1 where $R_3$, $R_4$, $R_5$, $R_6$, and $R_7$, and $Y_1$ are independently selected from —H, C1-C10 alkoxyl, C1-C10 polyalkoxyalkyl, C1-C20 polyhydroxyalkyl, C5-C20 polyhydroxyaryl, glucose derivatives of R groups, saccharides, amino, C1-C10 aminoalkyl, cyano, nitro, halogen, hydrophilic peptides, aryipolysulfonates, C1-C10 alkyl, C1-C10 aryl, —SO$_3$T, —CO$_2$T, —OH, —(CH$_2$)$_a$SO$_3$T, —(CH$_2$)$_a$OSO$_3$T, —(CH$_2$)$_a$NHSO$_3$T, —(CH$_2$)$_a$CO$_2$(CH$_2$)$_b$SO$_3$T, —(CH$_2$)$_a$OCO(CH$_2$)$_b$SO$_3$T, —(CH$_2$)$_a$CONH(CH$_2$)$_b$SO$_3$T, —(CH$_2$)$_a$NHCO(CH$_2$)$_b$SO$_3$T, —(CH$_2$)$_a$NHCONH (CH$_2$)$_b$SO$_3$T, —(CH$_2$)$_a$NHCSNH(CH$_2$)$_b$SO$_3$T, —(CH$_2$)$_a$OCONH(CH$_2$)$_b$SO$_3$T, —(CH$_2$)$_a$PO$_3$HT, —(CH$_2$)$_a$PO$_3$T$_2$, —(CH$_2$)$_a$OPO$_3$HT, —(CH$_2$)$_a$OPO$_3$T$_2$, —(CH$_2$)$_a$NHPO$_3$HT, —(CH$_2$)$_a$NHPO$_3$T$_2$, —(CH$_2$)$_a$CO$_2$ (CH$_2$)$_b$PO$_3$HT, —(CH$_2$)$_a$CO$_2$(CH$_2$)$_b$PO$_3$T$_2$, —(CH$_2$)$_a$OCO (CH$_2$)$_b$PO$_3$HT, —(CH$_2$)$_a$OCO(CH$_2$)$_b$PO$_3$T$_2$, —(CH$_2$)$_a$CONH(CH$_2$)$_b$PO$_3$HT, —(CH$_2$)$_a$CONH (CH$_2$)$_b$PO$_3$T$_2$, —(CH$_2$)$_a$NHCO(CH$_2$)$_b$PO$_3$HT, —(CH$_2$)$_a$NHCO(CH$_2$)$_b$PO$_3$T$_2$, —(CH$_2$)$_a$NHCONH(CH$_2$)$_b$PO$_3$HT, —(CH$_2$)$_a$NHCONH(CH$_2$)$_b$PO$_3$T$_2$, —(CH$_2$)$_a$NHCSNH (CH$_2$)$_b$PO$_3$HT, —(CH$_2$)$_a$NHCSNH(CH$_2$)$_b$PO$_3$T$_2$, —(CH$_2$)$_a$OCONH(CH$_2$)$_b$PO$_3$HT, —(CH$_2$)$_a$OCON H(CH$_2$)$_b$PO$_3$T$_2$, —CH$_2$(CH$_2$—O—CH$_2$)$_c$—CH$_2$—OH, —(CH$_2$)$_d$—CO$_2$T, —CH$_2$—(CH$_2$—O—CH$_2$)$_e$—CH$_2$—CO$_2$T, —(CH$_2$)$_f$—NH$_2$, —CH$_2$—(CH$_2$—O—CH$_2$)$_g$—CH$_2$—NH$_2$, —(CH$_2$)$_h$—N(R$_a$)—(CH$_2$)$_i$—CO$_2$T, and —(CH$_2$)$_j$—N(R$_b$)—CH$_2$—(CH$_2$—O—CH$_2$)$_k$—CH$_2$—CO$_2$T; where $W_1$ may be —CR$_c$R$_d$, —O—, —NR$_a$, —S—, or —Se; a, b, d, f, h, i, and j independently vary from 1-10; c, e, g, and k independently vary from 1-100; $R_a$, $R_b$, $R_c$, and $R_d$ are defined in the same manner as $Y_1$; and T is either H or a negative charge.

In one exemplary embodiment, the compound is an indole disulfonate falling within the class of compounds represented by Formula 1 and having the structure:

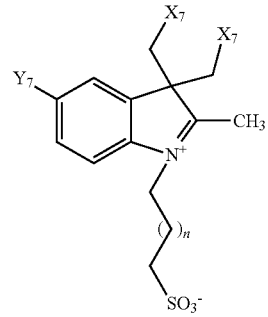

$n = 1-3$; $X_7 = OH$; $Y_7 = H$, $SO_3^-$, $CO_2H$, $CH_2CO_2H$, $CH_2OH$

In another exemplary embodiment, the compound is a polyhydroxyindole falling within the class of compounds represented by Formula 1 and having structures such as:

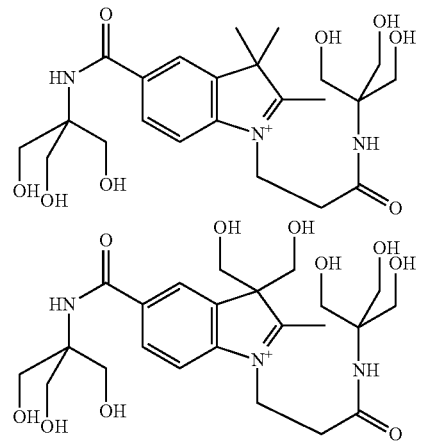

and

Methods for the synthetic preparation of such indole disulfonates and polyhydroxyindoles are described in U.S. Pat. No. 6,887,854.

In another group of embodiments, compounds for use as optical agents in the processes of the present invention correspond to Formula 2:

Formula 2

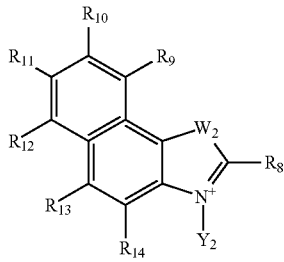

where $R_8$, $R_9$, $R_{10}$, $R_{11}$, $R_{12}$, $R_{13}$, $R_{14}$, and $Y_2$ are independently selected from —H, C1-C10 alkoxyl, C1-C10 polyalkoxyalkyl, C1-C20 polyhydroxyalkyl, C5-C20 polyhydroxyaryl, glucose derivatives of R groups, saccharides, amino, C1-C10 aminoalkyl, cyano, nitro, halogen, hydrophilic peptides, arylpolysulfonates, C1-C10 alkyl, C1-C10 aryl, —$SO_3T$, —$CO_2T$, —OH, —$(CH_2)_aSO_3T$, —$(CH_2)_aOSO_3T$, —$(CH_2)_aNHSO_3T$, —$(CH_2)_aCO_2(CH_2)_bSO_3T$, —$(CH_2)_aOCO(CH_2)_bSO_3T$, —$(CH_2)_aCONH(CH_2)_bSO_3T$, —$(CH_2)_aNHCO(CH_2)_bSO_3T$, —$(CH_2)_aNHCONH(CH_2)_bSO_3T$, —$(CH_2)_aNHCSNH(CH_2)_bSO_3T$, —$(CH_2)_aOCONNCH_2)_bSO_3T$, —$(CH_2)_aPO_3HT$, —$(CH_2)_aPO_3T_2$, —$(CH_2)_aOPO_3HT$, —$(CH_2)_aOPO_3T_2$, —$(CH_2)_aNHPO_3HT$, —$(CH_2)_aNHPO_3T_2$, —$(CH_2)_aCO_2(CH_2)_bPO_3HT$, —$(CH_2)_aCO_2(CH_2)_bPO_3T_2$, —$(CH_2)_aOCO(CH_2)_bPO_3HT$, —$(CH_2)_aOCO(CH_2)_bPO_3T_2$, —$(CH_2)_aCONH(CH_2)_bPO_3HT$, —$(CH_2)_aCONH(CH_2)_bPO_3T_2$, —$(CH_2)_aNHCO(CH_2)_bPO_3HT$, —$(CH_2)_aNHCO(CH_2)_bPO_3T_2$, —$(CH_2)_aNHCONH(CH_2)_bPO_3HT$, —$(CH_2)_aNHCONH(CH_2)_bPO_3T_2$, —$(CH_2)_aNHCSNH(CH_2)_bPO_3HT$, —$(CH_2)_aNHCSNH(CH_2)_bPO_3T_2$, —$(CH_2)_aOCONH(CH_2)_bPO_3HT$, and —$(CH_2)_aOCONH(CH_2)_bPO_3T_2$, —$CH_2(CH_2-O-CH_2)_c-CH_2-OH$, —$(CH_2)_d-CO_2T$, —$CH_2-(CH_2-O-CH_2)_a-CH_2-CO_2T$, —$(CH_2)_f-NH_2$, —$CH_2-(CH_2-O-CH_2)_9CH_2-NH_2$, —$(CH_2)_h-N(R_a)-(CH_2)_i-CO_2T$, and —$(CH_2)_j-N(R_b)-CH_2-(CH_2-O-CH_2)_k-CH_2-CO_2T$; $W_2$ is selected from —$CR_cR_d$, —O—, —$NR_c$, —S—, and —Se; a, b, d, f, h, i, and j independently vary from 1-10; c, e, g, and k independently vary from 1-100; $R_a$, $R_b$, $R_c$, and $R_d$ are defined in the same manner as $Y_2$; and T is either H or a negative charge.

In one exemplary embodiment, the compounds is a benzoindole disulfonate falling within the class of compounds represented by Formula 2 and having the structure:

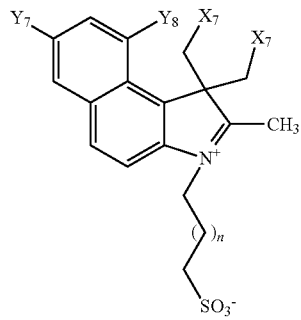

$n$ = 1-3; $X_7$ = H, OH; $Y_7$, $Y_8$ = H, $SO_3^-$, $CO_2H$, $CH_2CO_2H$, $CH_2OH$

Methods for the synthetic preparation of such benzoindole disulfonates are described in U.S. Pat. No. 6,887,854.

In yet another group of embodiments, cyanine dyes for use as optical agents in the processes of the present invention correspond to Formula 3:

Formula 3

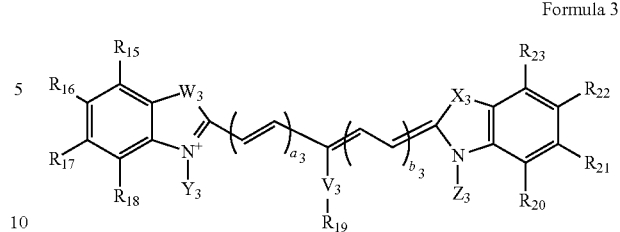

where $R_{15}$, $R_{16}$, $R_{17}$; $R_{18}$, $R_{19}$, $R_{20}$, $R_{21}$, $R_{22}$, $R_{23}$, $Y_3$, and $Z_3$ are independently selected from —H, C1-C10 alkoxyl, C1-C10 polyalkoxyalkyl, C1-C20 polyhydroxyalkyl, C5-C20 polyhydroxyaryl, glucose derivatives of R groups, saccharides, amino, C1-C10 aminoalkyl, cyano, nitro, halogen, hydrophilic peptides, arylpolysulfonates, C1-C10 alkyl, C1-C10 aryl, —$SO_3T$, —$CO_2T$, —OH, —$(CH_2)_aSO_3T$, —$(CH_2)_2OSO_3T$, —$(CH_2)_2OSO_3T$, —$(CH_2)_aNHSO_3T$, —$(CH_2)_aCO_2(CH_2)_bSO_3T$, —$(CH_2)_aOCO(CH_2)_bSO_3T$, —$(CH_2)_aCONH(CH_2)_bSO_3T$, $(CH_2)_aNHCO(CH_2)_bSO_3T$, —$(CH_2)_aNHCONH(CH_2)_bSO_3T$, —$(CH_2)_aNHCSNH(CH_2)_bSO_3T$, —$CH_2)_aOCONH(CH_2)_bSO_3T$, —$(CH_2)_aPO_3HT$, —$(CH_2)_aPO_3T_2$, —$(CH_2)_aOPO_3HT$, —$(CH_2)_aOPO_3T_2$, —$(CH_2)_aNHPO_3HT$, —$(CH_2)_aNHPO_3T_2$, —$(CH_2)_aCO_2(CH_2)_bPO_3HT$, —$(CH_2)_aCO_2(CH_2)_bPO_3T_2$, —$(CH_2)_aOCO(CH_2)_bPO_3HT$, —$(CH_2)_aOCO(CH_2)_bPO_3T_2$, —$(CH_2)_aCONH(CH_2)_bPO_3HT$, —$(CH_2)_aCONH(CH_2)_bPO_3T_2$, —$(CH_2)_aNHCO(CH_2)_bPO_3HT$, —$(CH_2)_aNHCO(CH_2)_bPO_3T_2$, —$(CH_2)_aNHCONH(CH_2)_bPO_3HT$, —$(CH_2)_aNHCONH(CH_2)_bPO_3T_2$, —$(CH_2)_aNHCSNH(CH_2)_bPO_3HT$, —$(CH_2)_aNHCSNH(CH_2)_bPO_3T_2$, —$(CH_2)_aOCONH(CH_2)_bPO_3HT$, and —$(CH_2)_aOCONH(CH_2)_bPO_3T_2$, —$CH_2(CH_2-O-CH_2)_c-CH_2-OH$, —$(CH_2)_d-CO_2T$, —$CH_2-(CH_2-O-CH_2)_e-CH_2-CO_2T$, —$(CH_2)_r-NH_2$, —$CH_2-(CH_2-O-CH_2)_g-CH_2-NH_2$, —$(CH_2)_h-N(R_a)-(CH_2)_i-CO_2T$, and —$(CH_2)_j-N(R_b)-CH_2-(CH_2-O-CH_2)_k-CH_2-CO_2T$; $W_3$ and $X_3$ are independently selected from —$CR_cR_d$, —O—, —S—, and —Se; $V_3$ is a single bond or is selected from —O—, —S—, —Se—, and —$NR_a$; a, b, d, f, h, i, and j independently vary from 1-10; c, e, g, and k independently vary from 1-100; $a_3$ and $b_3$ vary from 0 to 5; $R_a$, $R_b$, $R_c$, and $R_d$ are defined in the same manner as $Y_3$; T is either H or a negative charge.

In one exemplary embodiment, the cyanine dye is a polyhydroxyindole sulfonate falling within the class of compounds represented by Formula 3 and having the structure:

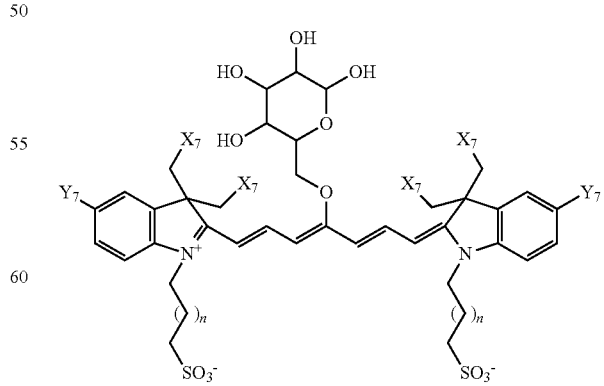

$n$ = 1-3; $X_7$ = H, OH; $Y_7$ = H, $SO_3^-$, $CO_2H$, $CH_2CO_2H$, $CH_2OH$

Methods for the preparation of such polyhydroxyindole sulfonates are described in U.S. Pat. No. 6,887,854.

In another group of embodiments, indocyanine dyes for use as optical agents in the processes of the present invention correspond to Formula 4:

Formula 4

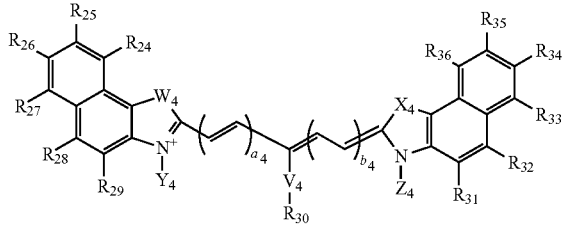

where $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $Y_4$, and $Z_4$ are independently selected from —H, C1-C10 alkoxyl, C1-C10 polyalkoxyalkyl, C1-C20 polyhydroxyalkyl, C5-C20 polyhydroxyaryl, glucose derivatives of R groups, saccharides, amino, C1-C10 aminoalkyl, cyano, nitro, halogen, hydrophilic peptides, arylpolysulfonates, C1-C10 alkyl, C1-C10 aryl, —$SO_3T$, —$CO_2T$, —OH, —$(CH_2)_aSO_3T$, —$(CH_2)_aOSO_3T$, —$(CH_2)_aNHSO_3T$, —$(CH_2)_aCO_2(CH_2)_bSO_3T$, —$(CH_2)_aOCO(CH_2)_bSO_3T$, —$(CH_2)_aCONH(CH_2)_bSO_3T$, —$(CH_2)_aNHCO(CH_2)_bSO_3T$, —$(CH_2)_aNHCONH(CH_2)_bSO_3T$, —$(CH_2)_aNHCSNH(CH_2)_bSO_3T$, —$(CH_2)_aOCONH(CH_2)_bSO_3T$, —$(CH_2)_aPO_3HT$, —$(CH_2)_aPO_3T_2$, —$(CH_2)_aOPO_3HT$, —$(CH_2)_aOPO_3T_2$, —$(CH_2)_aNHPO_3HT$, —$(CH_2)_aNHPO_3T_2$, —$(CH_2)_aCO_2(CH_2)_bPO_3HT$, —$(CH_2)_aCO_2(CH_2)_bPO_3T_2$, —$(CH_2)_aOCO(CH_2)_bPO_3HT$, —$(CH_2)_aO-COPH_2)_bPO_3T_2$, —$(CH_2)_aCONH(CH_2)_bPO_3HT$, —$(CH_2)_aCONH(CH_2)_aPO_3T_2$, —$(CH_2)_aNHCO(CH_2)_aPO_3HT$, —$(CH_2)_aNHCO(CH_2)_bPO_3T_2$, —$(CH_2)_aNHCONH(CH_2)_bPO_3HT$, —$(CH_2)_aNHCONH(CH_2)_bPO_3T_2$, —$(CH_2)_aNHCSNH(CH_2)_bPO_3HT$, —$(CH_2)_aNHCSNH(CH_2)_bPO_3T_2$, —$(CH_2)_aOCONH(CH_2)_bPO_3HT$, and —$(CH_2)_aOCONH(CH_2)_bPO_3T_2$, —$CH_2(CH_2—O—CH_2)_c—CH_2—OH$, —$(CH_2)_d—CO_2T$, —$CH_2—(CH_2—O—CH_2)_e—CH_2—CO_2T$, —$(CH_2)_f—NH_2$, —$CH_2—(CH_2—O—CH_2)_g—CH_2—NH_2$, —$(CH_2)_h—N(R_a)—(CH_2)_i—CO_2T$, and —$(CH_2)_j—N(R_b)—CH_2—(CH_2—O—CH_2)_k—CH_2—CO_2T$; $W_4$ and $X_4$ are independently selected from —$CR_cR_d$, —O—, —$NR_c$, —S—, and —Se; $V_4$ is a single bond or is selected from —O—, —S—, —Se—, and —$NR_a$; $a_4$ and $b_4$ vary from 0 to 5; a, b, d, f, h, i, and j independently vary from 1-10; c, e, g, and k independently vary from 1-100; $R_a$, $R_b$, $R_c$, and $R_d$ are defined in the same manner as $Y_4$; and T is either H or a negative charge.

In one exemplary embodiment, the indocyanine dye corresponding to Formula 4 is bis(ethylcarboxymethyl)indocyanine:

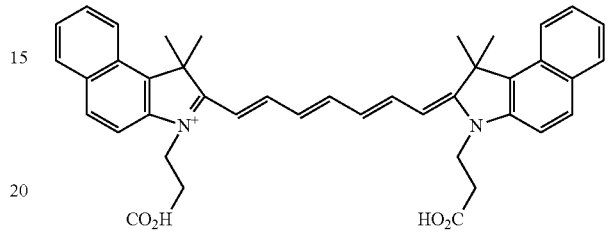

In another exemplary embodiment, the indocyanine dye corresponding to Formula 4 is bis(pentylcarboxymethyl) indocyanine:

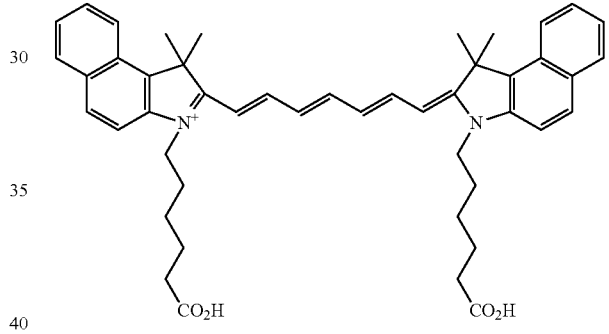

In yet another exemplary embodiment, the indocyanine dye is a polyhydroxyindole sulfonate falling within the class of compounds represented by Formula 4 and having the structure:

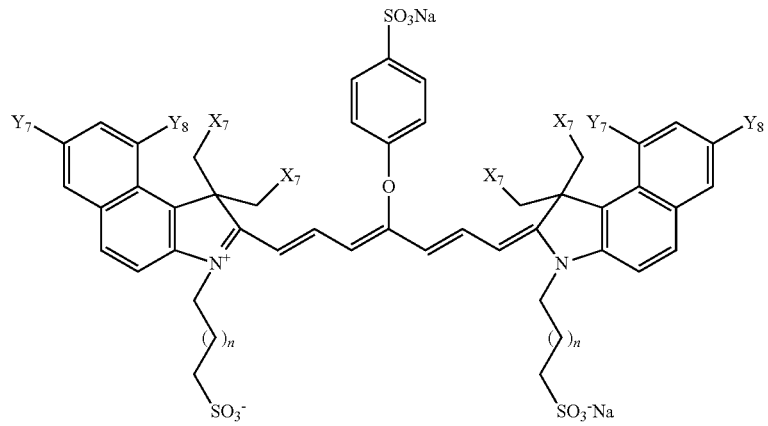

$n$ = 1-3; $X_7$ = H, OH; $Y_7$ = H, $SO_3^-$, $CO_2H$, $CH_2CO_2H$, $CH_2OH$

Methods for synthetic preparation of such polyhydroxyindole sulfonates, and for bis(ethylcarboxymethyl)indocyanine and bis(pentylcarboxymethyl)indocyanine, are described in U.S. Pat. No. 6,887,854.

In another exemplary embodiment, the indocyanine dye is an indocyaninebispropanoic acid dye (n=1) or an indocyaninebishexanoic acid dye (n=4) falling within the class of compounds represented by Formula 4 and having the structure:

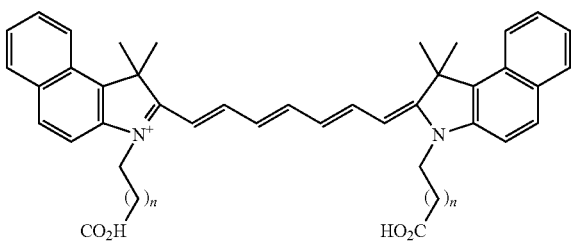 [SMILES: CC1(C)C(/C=C/C=C/C=C/C=C2/N(CCC(=O)O)c3ccc4ccccc4c3C2(C)C)=[N+](CCC(=O)O)c2ccc3ccccc3c21]

Methods for the synthetic preparation of indocyaninebispropanoic acid dye and of indocyaninebishexanoic acid dye are described in U.S. Pat. No. 6,761,878.

In yet another group of embodiments, cyanine dyes for use as optical agents in the processes of the present invention correspond to Formula 5:

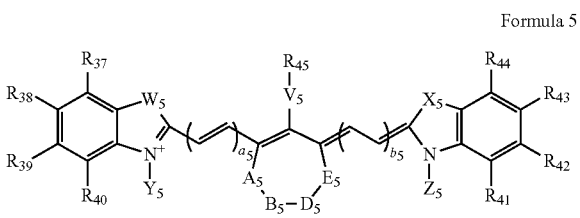

Formula 5 where $R_{37}$, $R_{38}$, $R_{39}$, $R_{40}$, $R_{41}$, $R_{42}$, $R_{43}$, $R_{44}$, $R_{45}$, $Y_5$, and $Z_5$ are independently selected from —H, C1-C10 alkoxyl, C1-C10 pofyalkoxyalkyl, C1-C20 polyhydroxyalkyl, C5-C20 polyhydroxyaryl, glucose derivatives of R groups, saccharides, amino, C1-C10 aminoalkyl, cyano, nitro, halogen, hydrophilic peptides, arylpolysulfonates, C1-C10 alkyl, C1-C10 aryl, —$SO_3T$, —$CO_2T$, —OH, —$(CH_2)_aSO_3T$, —$(CH_2)_aOSO_3T$, —$(CH_2)_aNHSO_3T$, —$(CH_2)_aCO_2(CH_2)_bSO_3T$, —$(CH_2)_aOCO(CH_2)_bSO_3T$, —$(CH_2)_aCONH(CH_2)_bSO_3T$, —$(CH_2)_aNHCO(CH_2)_bSO_3T$, —$(CH_2)_aNHCONH(CH_2)_bSO_3T$, —$(CH_2)_aNHCSNH(CH_2)_bSO_3T$, —$(CH_2)_aOCONH(CH_2)_bSO_3T$, —$(CH_2)_aPO_3HT$, —$(CH_2)_aPO_3T_2$, —$(CH_2)_aOPO_3HT$, —$(CH_2)_aOPO_3T_2$, —$(CH_2)_aNHPO_3HT$, —$(CH_2)_aNHPO_3T_2$, —$(CH_2)_aCO_2(CH_2)_bPO_3HT$, —$(CH_2)_aCO_2(CH_2)_bPO_3T_2$, —$(CH_2)_aOCO(CH_2)_bPO_3HT$, —$(CH_2)_aOCO(CH_2)_bPO_3T_2$, —$(CH_2)_aCONH(CH_2)_bPO_3HT$, —$(CH_2)_aCONH(CH_2)_bPO_3T_2$, —$(CH_2)_aNHCO(CH_2)_bPO_3HT$, —$(CH_2)_aNHCO(CH_2)_bPO_3T_2$, —$(CH_2)_aNHCONH(CH_2)_bPO_3HT$, —$(CH_2)_aNHCONH(CH_2)_bPO_3T_2$, —$(CH_2)_aNHCSNH(CH_2)_bPO_3HT$, —$(CH_2)_aNHCSNH(CH_2)_bPO_3T_2$, —$(CH_2)_aOCONH(CH_2)_bPO_3HT$, and —$(CH_2)_aOCONH(CH_2)_bPO_3T_2$, —$CH_2(CH_2—O—CH_2)_c—CH_2—OH$, —$(CH_2)_d—CO_2T$, —$CH_2—(CH_2—O—CH_2)_e—CH_2—CO_2T$, —$(CH_2)_f NH_2$, —$CH_2—(CH_2—O—CH_2)_g—CH_2—NH_2$, —$(CH_2)_h—N(R_a)—(CH_2)_i—CO_2T$, and —$(CH_2)_j—N(R_b)—CH_2—(CH_2—O—CH_2)_k—CH_2—CO_2T$; $W_5$ and $X_5$ are independently selected from —$CR_cR_d$, —O—, —$NR_c$, —S—, and —Se; $V_5$ is a single bond or is selected from —O—, —S—, —Se—, and —$NR_a$; $D_5$ is a single or a double bond; $A_5$, $B_5$ and $E_5$ may be the same or different and are independently selected from —O—, —S—, —Se—, —P—, —$NR_a$, —$CR_cR_d$, $CR_c$, alkyl, and —C=O; $A_5$, $B_5$, $D_5$, and $E_5$ may together form a 6 or 7 membered carbocyclic ring or a 6 or 7 membered heterocyclic ring optionally containing one or more oxygen, nitrogen, or a sulfur atom; a, b, d, f, h, i, and j independently vary from 1-10; c, e, g, and k independently vary from 1-100; $a_5$ and $b_5$ vary from 0 to 5; $R_a$, $R_b$, $R_c$, and $R_d$ are defined in the same manner as $Y_5$; and T is either H or a negative charge.

Methods for the synthetic preparation of such polyhydroxyindole sulfonates and rigid heteratomic indole sulfonate are described in U.S. Pat. No. 6,887,854.

In still another group of embodiments, indocyanine dyes for use as optical agents in the processes of the present invention correspond to Formula 6:

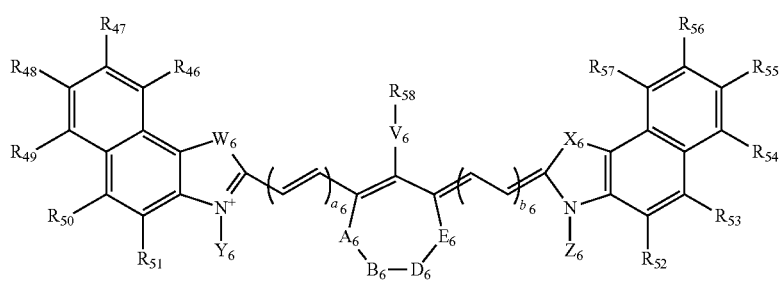

Formula 6 where $R_{46}$, $R_{47}$, $R_{48}$, $R_{49}$, $R_{50}$, $R_{51}$, $R_{52}$, $R_{53}$, $R_{54}$, $R_{55}$, $R_{56}$, $R_{57}$ and $R_{58}$, $Y_6$, and $Z_6$ are independently selected from —H, C1-C10 alkoxyl, C1-C10 polyalkoxyalkyl, C1-C20 polyhydroxyalkyl, C5-C20 polyhydroxyaryl, glucose derivatives of R groups, saccharides, amino, C1-C10 aminoalkyl, cyano, nitro, halogen, hydrophilic peptides, arylpolysulfonates, C1-C10 alkyl, C1-C10 aryl, —$SO_3T$, —$CO_2T$, —OH, —$(CH_2)_aSO_3T$, —$(CH_2)_aOSO_3T$, —$(CH_2)_aNHSO_3T$, —$(CH_2)_aCO_2(CH_2)_bSO_3T$, —$(CH_2)_aOCO(CH_2)_bSO_3T$, —$(CH_2)_aCONH(CH_2)_bSO_3T$, —$(CH_2)_aNHCO(CH_2)_bSO_3T$, —$(CH_2)_aNHCONH(CH_2)_bSO_3T$, —$(CH_2)_aNHCSNH(CH_2)_bSO_3T$, —$(CH_2)_aOCONH(CH_2)_bSO_3T$, —$(CH_2)_aPO_3HT$, —$(CH_2)_aPO_3T_2$, —$(CH_2)_aOPO_3HT$, —$(CH_2)_aOPO_3T_2$, —$(CH_2)_aNHPO_3HT$, —$(CH_2)_a$ $NHPO_3T_2$, —$(CH_2)_aCO_2(CH_2)_bPO_3HT$, —$(CH_2)_aCO_2$ $(CH_2)_bPO_3T_2$, —$(CH_2)_aOCO(CH_2)_bPO_3HT$, —$(CH_2)_a$ $OCO(CH_2)_bPO_3T_2$, —$(CH_2)_aCONH(CH_2)_bPO_3HT$, —$(CH_2)_aCONH(CH_2)_bPO_3T_2$, —$(CH_2)_aNHCO(CH_2)_b$ $PO_3HT$, —$(CH_2)_aNHCO(CH_2)_bPO_3T_2$, —$(CH_2)_aN$-$HCONH(CH_2)_bPO_3HT$, —$(CH_2)_aNHCONH(CH_2)_bPO_3T_2$, —$(CH_2)_aNHCSNH(CH_2)_bPO_3HT$, —$(CH_2)NHCSNH$ $(CH_2)_bPO_3T_2$, —$(CH_2)_aOCONH(CH_2)_bPO_3HT$, and —$(CH_2)_aOCONH(CH_2)_bPO_3T_2$, —$CH_2(CH_2$—$O$—$CH_2)_c$—$CH_2$—$OH$, —$(CH_2)_dCO_2T$, —$CH_2$—$(CH_2$—$O$—$CH_2)_b$—$CH_2$—$CO_2T$, —$(CH_2)_fNH_2$, —$CH_2$—$(CH_2$—$O$—$CH_2)_g$—$CH_2$—$NH_2$, —$(CH_2)_h$—$N(R_a)$—$(CH_2)_i$—$CO_2T$, and —$(CH_2)_j$—$N(R_b)$—$CH_2(CH_2$—$O$—$CH_2)_k$—$CH_2$—$CO_2T$, $W_6$ and $X_6$ are independently selected from the group consisting of —$CR_cR_d$, —$O$—, —$S$—, and —$Se$; $V_6$ is a single bond or is selected from the group consisting of —$O$—, —$S$—, —$Se$—, and —$NR_a$; $D_6$ is a single or a double bond; $A_6$, $B_6$ and $E_6$ may be the same or different and are selected from —$O$—, —$S$—, —$Se$—, —$P$—, —$NR_a$, —$CR_cR_d$, $CR_c$, alkyl, and —$C$=$O$; $A_6$, $B_6$, $D_6$, and $E_e$ may together form a 6 or 7 membered carbocyclic ring or a 6 or 7 membered heterocyclic ring optionally containing one or more oxygen, nitrogen, or sulfur atom; a, b, d, f, h, i, and j independently vary from 1-10; c, e, g, and k independently vary from 1-100; $a_6$ and $b_6$ vary from 0 to 5; $R_a$, $R_b$, $R_c$, and $R_d$ are defined in the same manner as $Y_6$; and T is either H or a negative charge.

In one exemplary embodiment, the indocyanine dye is a polyhydroxylbenzoindole sulfonate falling within the class of compounds represented by Formula 6 and having the structure:

In still yet another group of embodiments, pyrazine derivatives for use as optical agents in the processes of the present invention correspond to Formula 7:

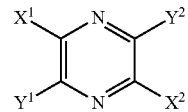

Formula 7

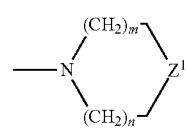

Formula A where of $X^1$ and $X^2$ is characterized as an electron withdrawing substituent and is independently selected from —$CN$, —$CO_2R^1$, —$CONR^2R^3$, —$COR^4$, —$NO_2$, —$SOR^5$, —$SO_2R^6$, —$SO_2OR^7$ and/or —$PO_3R^8R^9$. Each of $Y^1$ and $Y^2$ is characterized as an electron donating substituent and is independently selected from —$OR^{19}$, —$SR^{11}$, —$NR^{12}R^{13}$, —$N(R^{14})COR^{15}$ and/or substituents corresponding to Formula A below. $Z^1$ is a direct bond, —$CR^{16}R^{17}$—, —$O$—, —$NR^{18}$—, —$NCOR^{19}$—, —$S$—, —$SO$— or —$SO_2$—. "m" and "n" are any appropriate integers between and including 1 and 6, and in one embodiment are any integers between and including 1 and 3. $R^1$ to $R^{19}$ are any suitable substituents

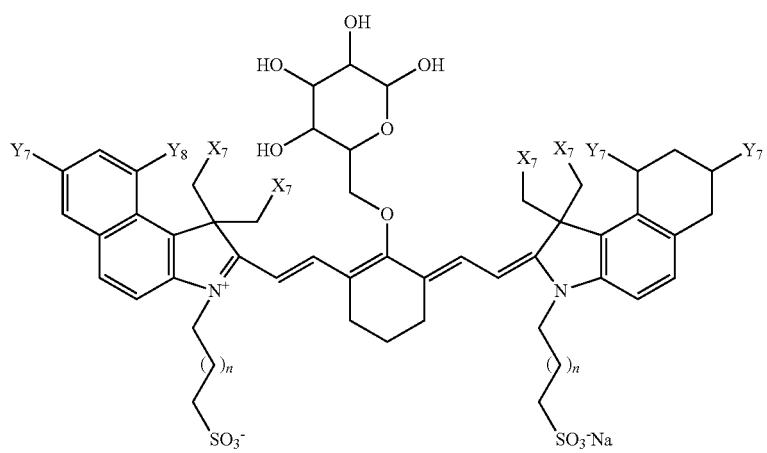

$n = 1\text{-}3$; $X_7 = H$, $OH$; $Y_7$, $Y_8 = H$, $SO_3^-$, $CO_2H$, $CH_2CO_2H$, $CH_2OH$ A method for synthetic preparation of such polyhydroxylbenzoindole sultanates is described in U.S. Pat. No. 6,887,854.

A hydrophilic chelating agent, such as ethylenediaminetetraacetic acid (EDTA), diethylenetriaminepentaacetic acid (DPTA), 1,4,7,10-tetraazacyclododecanetetraacetic acid (DOTA), or their derivatives, can be attached to compounds of Formulas 1-6 as one or more R groups. These structures are expected to be highly water soluble.

capable of enhancing biological and/or physicochemical properties of the pyrazine derivatives. For example, each of the R groups of $R^1$ to $R^{19}$ may independently be any one of a hydrogen atom, an anionic functional group (e.g., carboxylate, sultanate, sulfate, phosphonate and phosphate), and/or a hydrophilic functional group (e.g., hydroxyl, carboxyl, sulfonyl, sulfonato and phosphonato).

In one exemplary embodiment, the pyrazine derivative corresponding to Formula 7 is 3,6-dicyano-2,5-[(N,N,N',N'-tetrakis(carboxymethyl)amino]pyrazine:

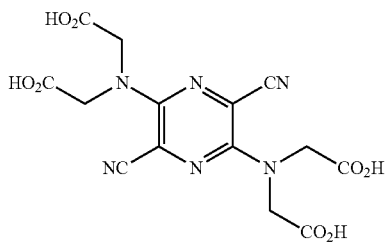 [SMILES: N#Cc1nc(N(CC(=O)O)CC(=O)O)c(C#N)nc1N(CC(=O)O)CC(=O)O]

In another exemplary embodiment, the pyrazine derivative corresponding to Formula 7 is 3,6-[(N,N,N',N'-tetrakis (2-hydroxyethyl)amino]pyrazine-2,5-dicarboxylic acid:

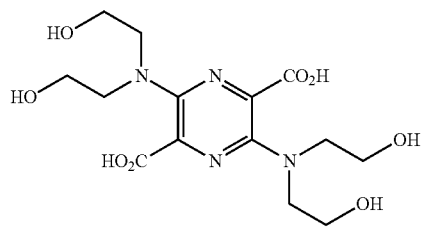 [SMILES: O=C(O)c1nc(N(CCO)CCO)c(C(=O)O)nc1N(CCO)CCO]

In yet another exemplary embodiment, the pyrazine derivative corresponding to Formula 7 is 3,6-bis(N-azatedino)pyrazine-2,5-dicarboxylic acid:

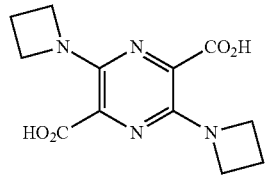 [SMILES: O=C(O)c1nc(N2CCC2)c(C(=O)O)nc1N1CCC1]

In another exemplary embodiment, the pyrazine derivative corresponding to Formula 7 is 3,6-bis(N-morpholino) pyrazine-2,5-dicarboxylic acid:

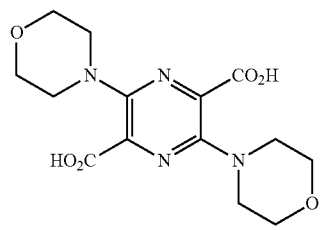 [SMILES: O=C(O)c1nc(N2CCOCC2)c(C(=O)O)nc1N1CCOCC1]

In another exemplary embodiment, the pyrazine derivative corresponding to Formula 7 is 3,6-bis(N-piperazino) pyrazine-2,5-dicarboxylic acid:

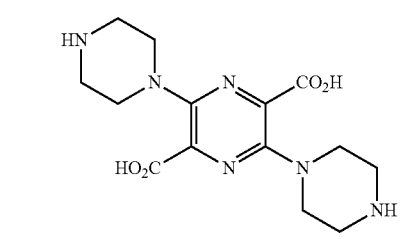 [SMILES: O=C(O)c1nc(N2CCNCC2)c(C(=O)O)nc1N1CCNCC1]

In another exemplary embodiment, the pyrazine derivative corresponding to Formula 7 is 3,6-bis(N-thiomorpholino)pyrazine-2,5-dicarboxylic acid:

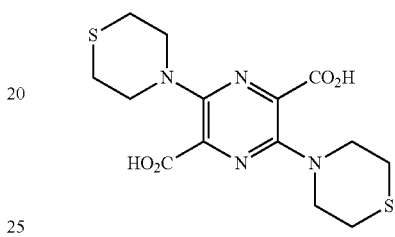

In yet another exemplary embodiment, the pyrazine derivative corresponding to Formula 7 is 3,6-bis(N-thiomorpholino)pyrazine-2,5-dicarboxylic acid S-oxide:

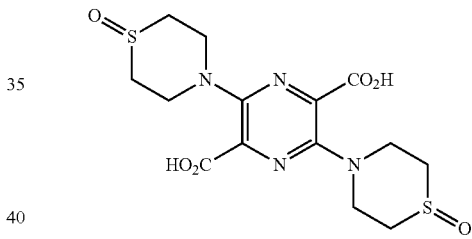

In another exemplary embodiment, the pyrazine derivative corresponding to Formula 7 is 2,5-dicyano-3,6-bis(N-thiomorpholino)pyrazine S,S-dioxide:

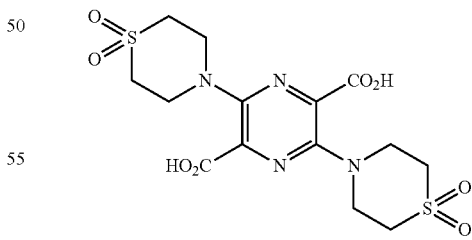

Methods for the synthetic preparation of these pyrazine derivatives are described in U.S. Patent Application Ser. No. 60/815,712 and PCT published application WO 2006/071759.

In yet another group of embodiments, pyrazine derivatives for use as optical agents in the processes of the present invention correspond to Formula 8:

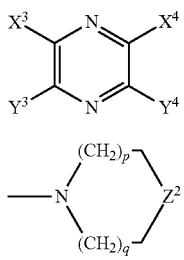

Formula 8

Formula B where each of $X^3$ and $X^4$ is characterized as an electron withdrawing substituent and is independently selected from —CN, —$CO_2R^{20}$, —$CONR^{21}R^{22}$, —$COR^{23}$, —$NO_2$, —$SOR^{24}$, —$SO_2R^{28}$, —$SO_2OR^{26}$ and/or $PO_3R^{27}R^{28}$. Each of $Y^3$ and $Y^4$ is characterized as an electron donating substituent and is independently selected from —$OR^{29}$, —$SR^{30}$, —$NR^{31}R^{32}$, —$N(R^{32})COR^{34}$ and/or substituents corresponding to Formula B below. $Z^2$ is a direct bond, $CR^{35}R^{36}$—, —O—, —$NR^{37}$—, —$NCOR^{38}$—, —S—, —SO— or —$SO_2$—. "p" and "q" are any appropriate integers between and including 1 and 6, and in one embodiment are integers between and including 1 and 3. $R^{20}$ to $R^{38}$ are any appropriate substituents capable of enhancing biological and/or physicochemical properties of the pyrazine derivatives of Formula 8. For example, each of the R groups of $R^{20}$ to $R^{38}$ may independently be any one of a hydrogen atom, an anionic functional group (e.g., carboxylate, sulfonate, sulfate, phopshonate and phosphate), and/or a hydrophilic functional group (e.g., hydroxyl, carboxyl, sulfonyl, sulfonato and phosphonato).

Other optical agents that may be used as optical agents in the processes of the present invention include, but are not limited to, for example, florescein-polyaspartic acid (6000) conjugates, fluorescein-polyaspartic acid (10000) conjugates, fluorescein-polyglutamic acid (13000) conjugates, fluorescein-polyarginine (10000) conjugates, indocyanine-dodecaaspartic acid conjugates, and indocyanine (NIRD)-polyaspartic acid 6000 conjugates. Methods for the preparation of these compounds are described in U.S. Pat. No. 6,228,344.

III. Routes of Administration

Effective amounts of one or more optical agents can be administered to a surgical patient by any one of various processes known in the art. An optical agent may be administered parenterally or enterally. In one embodiment, one or more optical agents are administered systemically for delivery to the renal system of a patient. For example, optical agents can be administered to a patient intravenously, intraarterially, orally, via a gastric or intestinal (e.g., duodenal or jejunal) feeding tube, by intramuscular injection, by subcutaneous injection or infusion, by intraperitoneal injection or infusion, intrathecally, sublingually, rectally, vaginally, nasally, by inhalation, by transdermal absorption through the skin, or by intraosseous infusion.

Intravenous administration may be used to deliver a single dose or bolus of one or more optical agents. Alternatively, intravenous administration of the optical agent(s) can be intermittent or continuous.

In another embodiment, the optical agents are administered locally to a patient's renal system or a tissue thereof via an appropriate delivery device. For example, one or more optical agents may be injected into a tissue of the renal system. As another example, one or more optical agents may be infused or instilled into the bladder via a urinary catheter. Infusion or instillation of an optical agent into the bladder via a urinary catheter may be preferred where urinary catheterization is required or desirable for other reasons (e.g., to drain urine while a patient is under anesthesia). Infusion or instillation of optical agents into the bladder via a urinary catheter may also facilitate detection of the urethra.

The delay between administration of the optical agent(s) and appearance of the optical agent(s) in a patient's renal system will vary depending on the specific optical agent(s) involved, the route of administration, the route by which the agent is primarily excreted (i.e., renal or hepatobiliary) and the like.

Administration of more than one optical agent to a surgical patient can be accomplished by administering a formulation (e.g., a sterile solution for intravenous or intraperitoneal administration) containing all of the optical agents to be administered. Alternatively, each optical agent may be administered in a separate formulation. When more than one optical agent is administered to a patient, administration of each agent need not be via the same route (e.g., one agent could be administered by infusion into the bladder via a urinary catheter while another is administered intravenously). Administration of multiple optical agents may be, but need not be, simultaneous.

In some embodiments of the invention, the renally excretable optical agents may be co-administered with other biocompatible compounds.

IV. Formulations

The renally excretable optical agents can be formulated into compositions for enteral or parenteral administration to a patient. In general, such compositions contain an effective amount of one or more optical agents, along with pharmaceutical carriers and excipients appropriate for the desired route of administration. The composition may thus contain a single optical agent or may contain a combination of two or more optical agents for co-administration to a patient.

In one embodiment, the optical agent(s) is/are formulated as sterile aqueous solutions or suspensions for parenteral administration. Such parenteral solutions or suspensions may be injected directly or mixed with a large volume parenteral composition for systemic administration. Exemplary routes for administration of such solutions include intravenous administration, intraperitoneal injection or infusion, or infusion into the bladder via a urinary catheter.

Sterile aqueous solutions or suspensions for parenteral administration which contain one or more renally excretable optical agents may also optionally contain one or more of the following components: pharmaceutically acceptable buffers, electrolytes (e.g., sodium chloride), diluents, solvents, antimicrobial agents, chelating agents (e.g., ethylenediaminetetraacetic acid (EDTA)), preservatives, surfactants, and/or any other appropriate biocompatible compound.

In another embodiment, the optical agents may be formulated for enteral administration, for example, as sterile aqueous solutions or suspensions or as solids. Optical agents formulated in a sterile aqueous solution or suspension for enteral administration may be administered, for instance, orally or via a feeding tube. Such solutions or suspensions may also optionally contain one or more of the following components in addition to the optical agent(s): pharmaceutically acceptable buffers, electrolytes (e.g., sodium chloride), diluents, solvents, antimicrobial agents, chelating agents (e.g., ethylenediaminetetraacetic acid (EDTA)), preservatives, surfactants, thixotropic agents, and/or any other appropriate biocompatible compound. Aqueous solutions for oral administration may also optionally contain flavoring agents and/or other ingredients for enhancing their organoleptic qualities.

The optical agents may also be formulated as solids for oral administration. For example, the optical agents may be enclosed in capsules or compressed into tablets. Solid formulations for oral administration containing one or more renally excretable optical agents may also optionally contain one or more of the following components: binders (e.g., a starch, sugar, cellulose, or sugar alcohol), fillers (e.g., a plant cellulose, dibasic calcium phosphate, soybean oil, or safflower oil), disintegrants, lubricants (e.g., stearic acid or magnesium stearate), coatings (e.g., cellulose or a synthetic polymer), sweeteners or other flavoring agents, preservatives, and/or any other appropriate biocompatible compound.

In yet another embodiment, the optical agents may be formulated as solids to be reconstituted into a sterile aqueous solution or suspension prior to administration.

The optical agents may be formulated in liposomes, micelles, microspheres, or microcapsules. Preparation and loading may be accomplished by processes well known in the art.

V. Dosing

The amount of an optical agent administered for a surgical procedure will typically depend upon the optical agent administered, the route of administration, the means employed for detection, the tissue(s) to be delimited, the degree of fluorescence desired, and the surgical method employed. By way of example, dosages may typically range from about 0.05 µm/kg body weight to about 20 µm/kg of body weight.

VI. Kit

For convenience, optical agents for use in accordance with the processes of the present invention may be provided to the user in the form of a kit containing some or all of the necessary components. The kit may include one or more of the following components: (i) one or more optical agents, (ii) means for administration (e.g., syringe), and (iii) instructions for using the composition to optically detect one or more tissues of the renal system of a surgical patient. The kit may also optionally contain buffers, excipients, salts, preservatives, and the like.

In one embodiment, the optical agent is provided in the kit as a sterile aqueous solution or suspension that can be administered, for example, intravenously, by infusion into the bladder via a urinary catheter, by intraperitoneal injection or infusion, or in any other appropriate manner. Alternatively, the optical agent may be provided in the kit as a sterile aqueous solution or suspension for oral administration. In yet another embodiment, the optical agent may be provided in the kit as a solid composition (e.g., a tablet or capsule) that can be administered orally. In yet another embodiment, the optical agent may be provided in the kit as a solid formulation for reconstitution into a sterile aqueous solution or suspension prior to administration to a surgical patient.

The instructions of the kit of the present invention may include, for example, information about the optical agent(s) (e.g., dosage information, optimal absorption or excitation wavelengths, optimal detection wavelengths, renal clearance kinetics, optimal timing of administration with relation to the surgical procedure, and the like), information regarding any other compounds included in the formulation (e.g., buffers, diluents, preservatives, etc., as described above), instructions for reconstituting a solid biocompatible composition included in the kit, instructions for administering the biocompatible composition of the kit to a surgical patient, instructions for detecting an optical agent following administration to a surgical patient, instructions for optimizing detection of the optical agent(s), and/or instructions for determining the extent of renal excretion of the optical agent(s).

The following examples are provided in order to more fully illustrate the present invention.

EXAMPLES

Example 1

Renal Clearance of 3,6-Diaminopyrazine-2,5-Dicarboxylic Acid in an Intact Rat

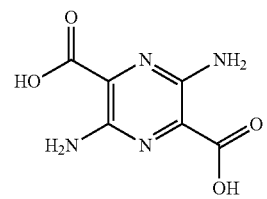

Incident laser light having a wavelength of about 470 nm was delivered via a fiber optic bundle to the ear of an anesthetized intact Sprague-Dawley rat. A photodetector was used to detect fluorescence from within the ear. A background reading of fluorescence was obtained prior to administration of optical agent. A pyrazine agent (2 ml of a 0.4 mg/ml solution of 3,6-diaminopyrazine-2,5-dicarbonyl acid in PBS) was then administered to the rat by a bolus injection into the lateral tail vein. As shown in FIG. 1, after injection, the fluorescence signal rapidly increased to a peak value, then decayed as a function of time, indicating the agent was cleared from the bloodstream over a period of slightly over twenty minutes.

The blood clearance time profile likely followed a two compartment pharmacokinetic model. The fluorescent signal arising from the agent concentration in the blood as a function of time was therefore fit to a double exponential decay. The equation employed to fit the data was:

$$S = Ae^{-t/\tau_1} + Be^{-t/\tau_2} + C \quad (1)$$

where S is the fluorescent light intensity signal measured, and t is the time point of the measurement. The decay times $\tau_1$ and $\tau_2$, and the constants A, B, and C were deduced from the fitting procedure. The non-linear regression analysis package in SigmaPlot® (Systat Software Inc., Richmond Calif.) was used to fit data to Eq. (1). In this and the following example, $\tau_1$ represents the time constant for vascular-extracellular fluid equilibrium, and $\tau_2$ represents optical agent clearance from the blood.

Example 2

Figure 2:
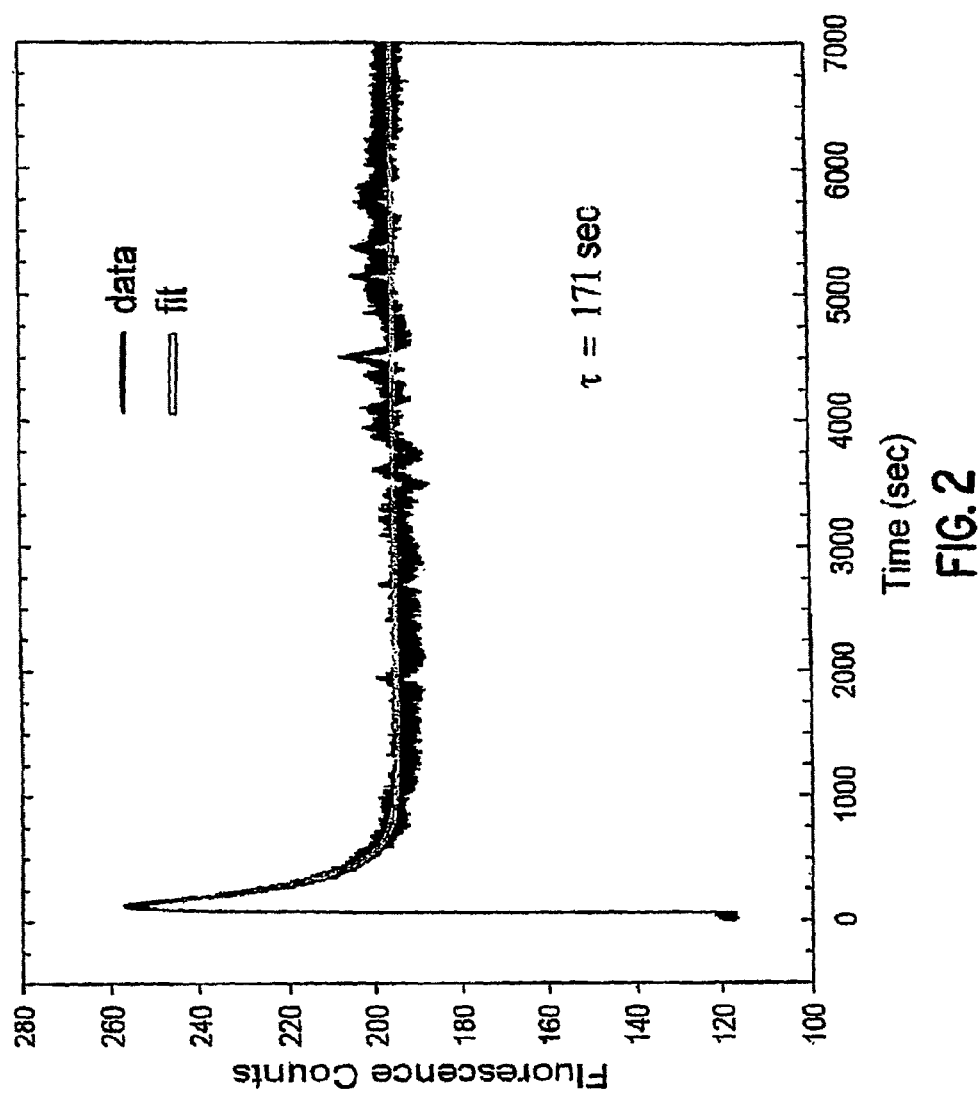
FIG. 2 shows the renal clearance of an optical agent (3,6-diaminopyrazine-2,5-dicarboxylic acid) in a bilaterally nephrectomized rat. Data were generated in accordance with the procedures set forth in Example 2.

Renal Clearance of 3,6-Diaminopyrazine-2,5-Dicarboxylic Acid in a Bilaterally Nephrectomized Rat An anesthetized Sprague-Dawley rat was bilaterally nephrectomized. Incident laser light having a wavelength of about 470 nm was delivered via a fiber optic bundle to the ear of the rat. A photodetector was used to detect fluorescence from within the ear. A background reading of fluorescence was obtained prior to administration of the pyrazine agent. The pyrazine agent (2 ml of a 0.4 mg/ml solution of 3,6-diaminopyrazine-2,5-dicarbonyl acid in PBS) was then administered to the rat by a bolus injection into the lateral tail vein. As shown in FIG. 2, shortly after the injection, the detected fluorescence signal rapidly increased to a peak value. However, the pyrazine agent was not cleared because the blood supply to the kidneys, the organ through which excretion would occur, had been arrested. Specifically, the renal arteries were tied off to block blood flow to the kidneys. The failure of the pyrazine agent to clear from the blood of the bilaterally nephrectomized rat indicated that the agent was renally excretable.

Figure 3:
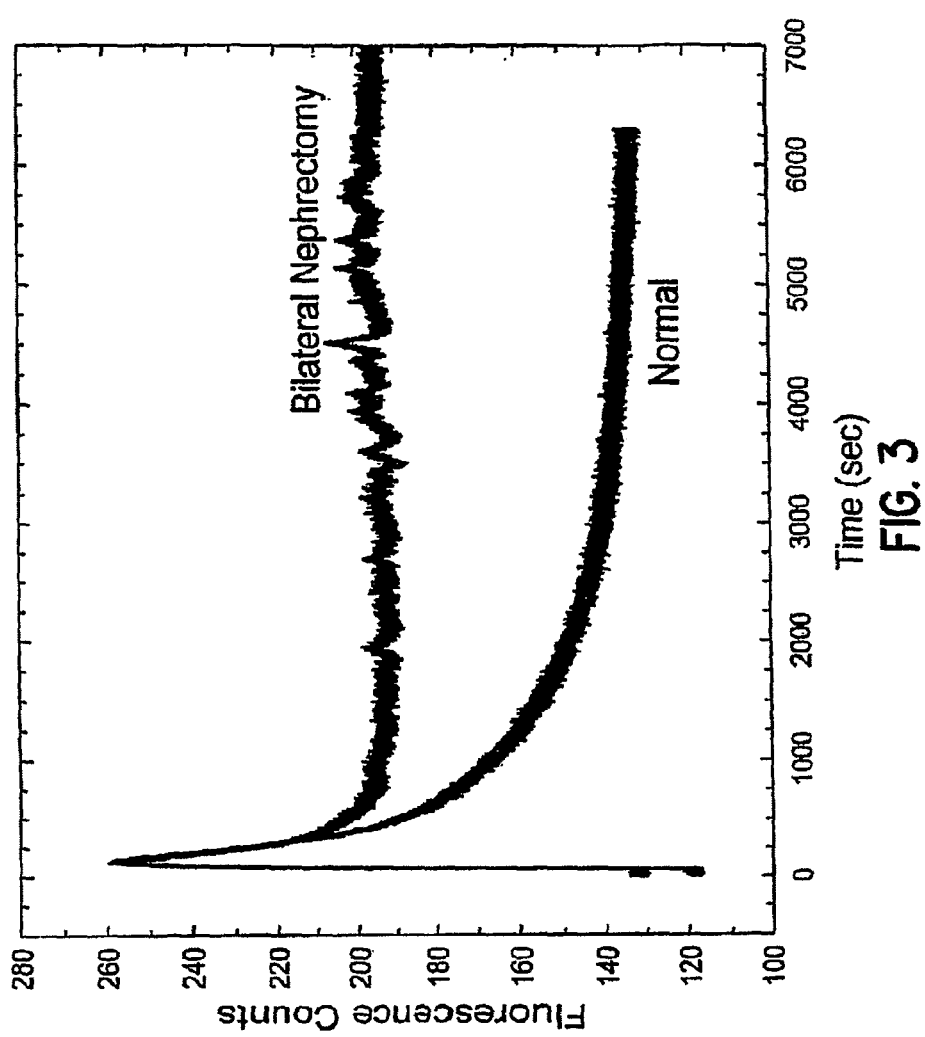
FIG. 3 shows a comparison of the data from FIGS. 1 and 2.

A comparison of clearance data from the intact rat (FIG. 1) and the bilaterally nephrectomized rat (FIG. 2) is shown in FIG. 3. Experiments similar to those shown in FIGS. 1 and 2 can be used to determine whether or not a candidate agent is renally excretable.

Example 3

Detection of 3,6-Diaminopyrazine-2,5-Dicarboxylic Acid in a Rat Ureter

A Sprague-Dawley rat was anesthetized with a cocktail of ketamine (87 mg/kg) and xylazine (2.6 mg/kg) administered by intraperitoneal injection. After the animal had achieved the desired plane of anesthesia, a 25 gauge butterfly with 3" tubing was placed in the lateral tail vein of the animal and flushed with saline. The rat was placed onto a heating pad and kept warm throughout the study.

An abdominal incision was made to access the ureters and expose the ureters to a laser having the appropriate wavelength to cause the optical agent employed to fluoresce. Data acquisition was initiated, and a background reading of fluorescence was obtained prior to administration of the optical agent.

The optical agent, 3,6-diaminopyrazine-2,5-dicarboxylic acid, was administered to the rat by a bolus injection into the lateral tail vein and traveled through the circulatory system and kidneys to reach the ureters. The dose of optical agent was about 2 mL of 0.4 mg/mL solution in PBS. The rat weighed approximately 250 g.

Figure 4:
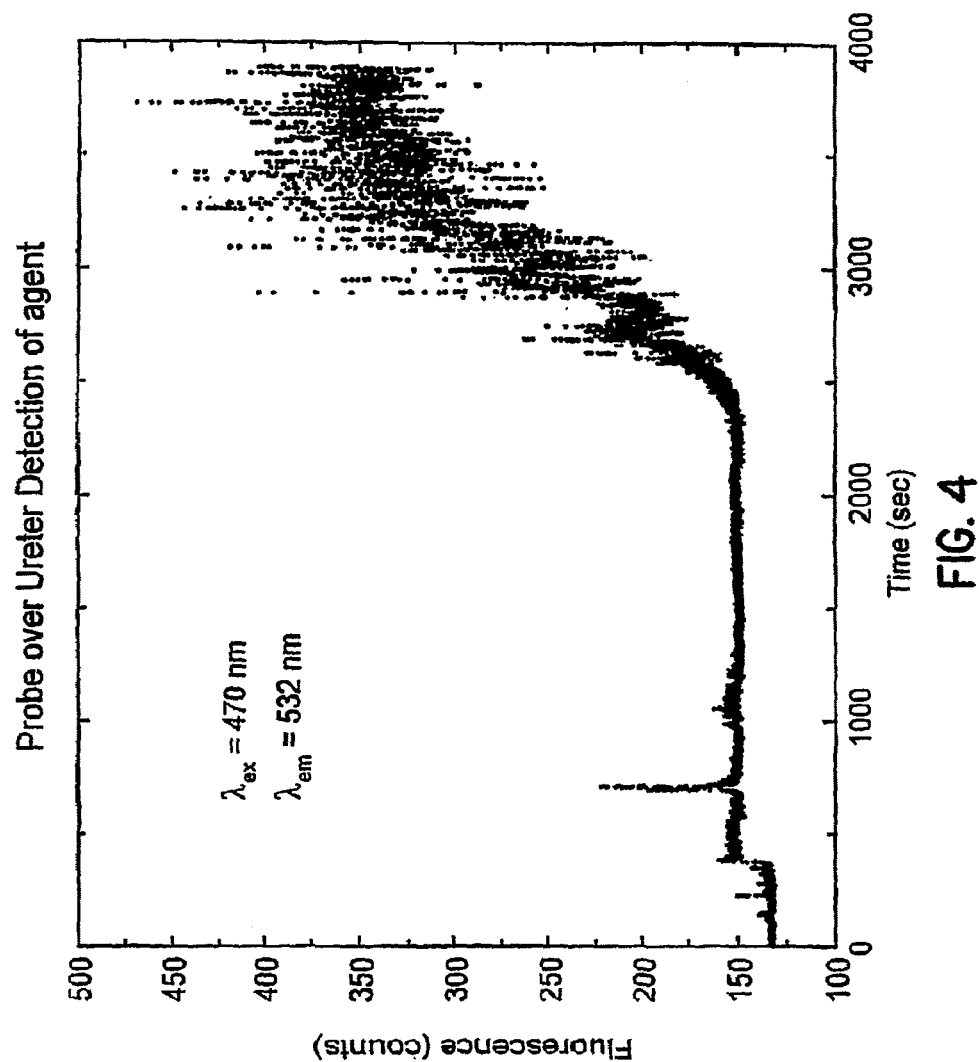
FIG. 4 shows the fluorescence of an optical agent (3,6-diaminopyrazine-2,5-dicarboxylic acid) in the ureter of an intact rat. Data were generated in accordance with the procedures set forth in Example 3.
Figure 5:
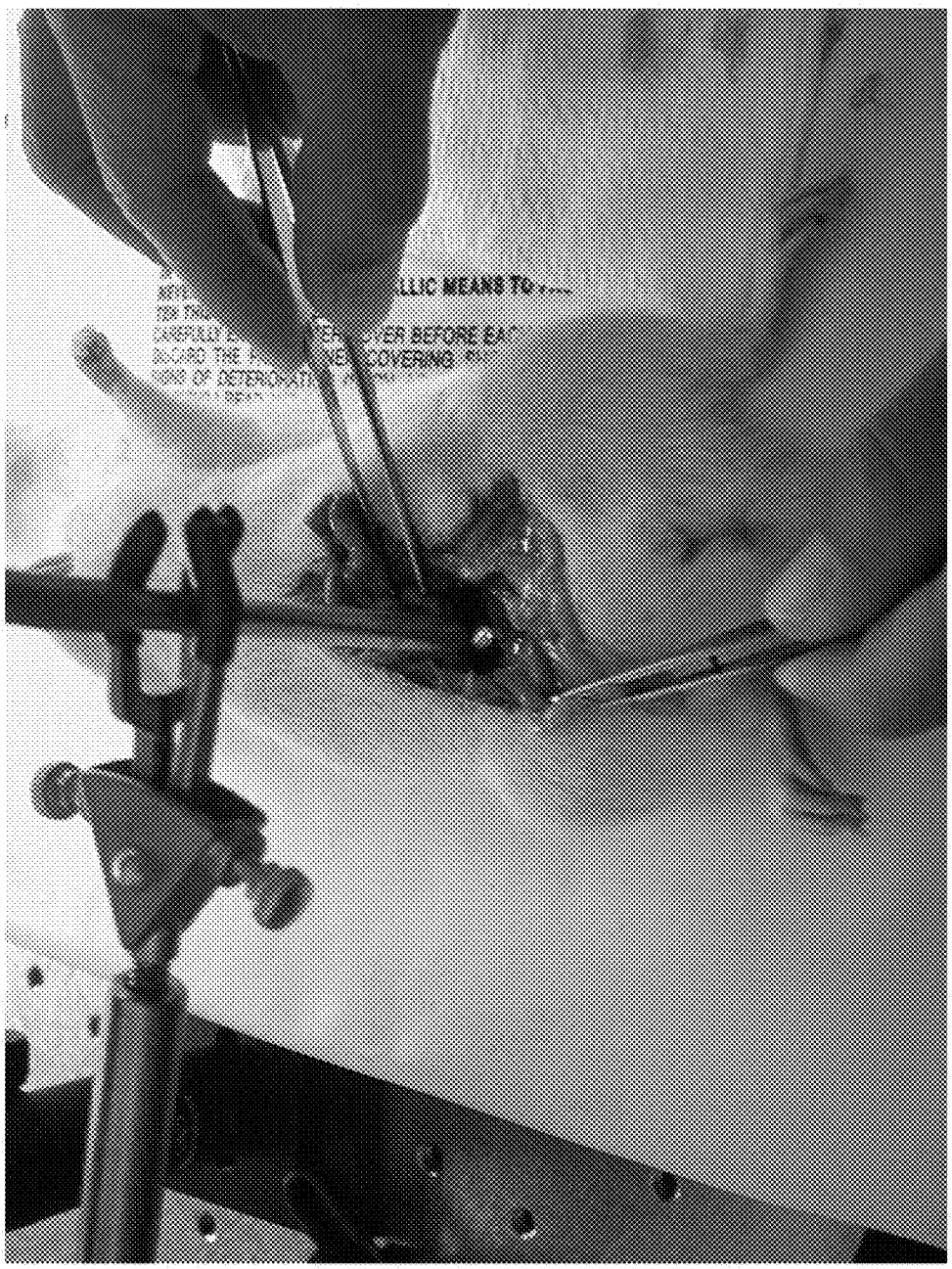
FIG. 5 is a color photograph of a surgical field, showing a fluorescing optical agent (3,6-diaminopyrazine-2,5-dicarboxylic acid) in the ureter of an intact rat. The optical agent was administered in accordance with the procedures set forth in Example 3.
Figure 6:
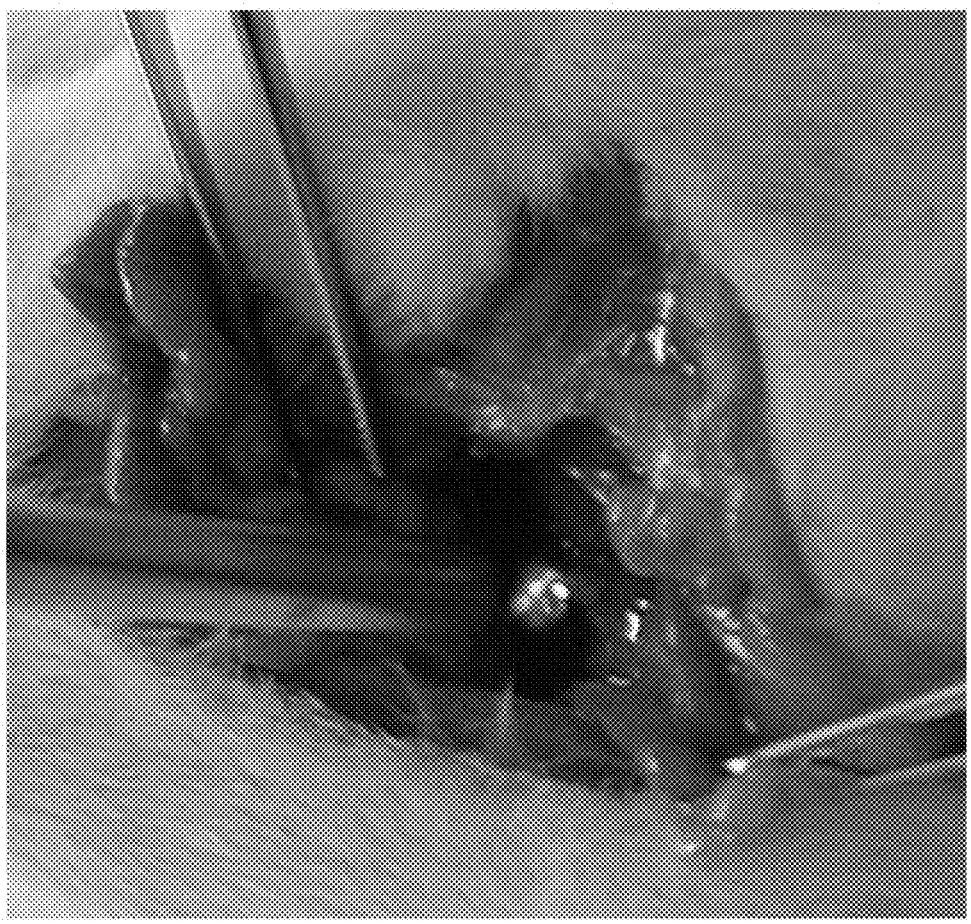
FIG. 6 is a magnified view of a portion of the color photograph of FIG. 5.
Figure 7:
FIG. 7 is another color photograph of a surgical field, taken in the presence of a 500 nm long pass filter and showing a fluorescing optical agent (3,6-diaminopyrazine-2,5-dicarboxylic acid) in the ureter of an intact rat. The optical agent was administered in accordance with the procedures set forth in Example 3.

A 3 mW laser from Power Technology, Inc. (Little Rock, Ark.) was used to emit light into one end of a fiber optic bundle, the other end of the bundle being positioned adjacent the ureter. As shown in FIG. 4, fluorescence from the optical agent within the ureter was detected about 40 minutes after intravenous administration of the optical agent. Fluorescence was only observed from the ureter and not from any surrounding tissue, indicating that the optical agent was confined within the ureter and was not present in surrounding tissues. As shown in FIGS. 5-6, when the surgical field was exposed to incident light having a wavelength of about 470 nm, the optical agent within the ureters emitted fluorescent energy at a wavelength of about 530 nm. Images of the surgical field showing the fluorescing optical agent in the ureter are shown in FIGS. 5-6 (in the absence of a 500 nm long pass filter) and FIG. 7 (in the presence of a 500 nm long pass filter).

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results are attained.

As various changes could be made in the above processes and compositions without departing from the scope of the invention, it is intended that all matter contained in the above description and shown in any accompanying figures shall be interpreted as illustrative and not in a limiting sense.

What is claimed is:

1. A process for using a fluorescent agent in a surgical procedure, the process comprising:
    administering a renally excretable fluorescent agent into the bloodstream of a patient, wherein the renally excretable optical agent is selected from the group consisting of phenylxanthenes, phenothiazines, phenoselenazines, cyanines, indocyanines, squaraines, dipyrrolo pyrimidones, anthraquinones, tetracenes, quinolines, pyrazines, acridines, acridones, phenanthridines, azo dyes, rhodamines, phenoxazines, azulenes, azaazulenes, triphenyl methane dyes, indoles, benzoindoles, indocarbocyanines, benzoindocarbocyanines, derivatives having the general structure of 4,4-difluoro-4-bora-3a,4a-diaza-s-indacene, and conjugates thereof and derivatives thereof;
    irradiating a ureter of the patient's renal system with infrared radiation, visible radiation, ultraviolet radiation or combinations thereof to excite the agent in the patient's urine and cause the agent to fluoresce; and
    detecting the agent's fluorescence in the irradiated ureter to demarcate the position of the ureter and distinguish the ureter from the surrounding tissue during the surgical procedure, wherein the surgical procedure is selected from an abdominal surgery and a pelvic surgery.

2. A process for using a fluorescent agent in a surgical procedure, the process comprising:
    irradiating a surgical field of a patient undergoing an abdominal surgery with infrared radiation, visible radiation, ultraviolet radiation or combinations thereof to excite a renally excretable fluorescent agent in the patient's urine and cause the agent to fluoresce, which is located in a ureter of the patient's renal system in the surgical field during the irradiating, wherein the renally excretable optical agent is selected from the group consisting of phenylxanthenes, phenothiazines, phenoselenazines, cyanines, indocyanines, squaraines, dipyrrolo pyrimidones, anthraquinones, tetracenes, quinolines, pyrazines, acridines, acridones, phenanthridines, azo dyes, rhodamines, phenoxazines, azulenes, azaazulenes, triphenyl methane dyes, indoles, benzoindoles, indocarbocyanines, benzoindocarbocyanines, derivatives having the general structure of 4,4-difluoro-4-bora-3a,4a-diaza-s-indacene, and conjugates thereof and derivatives thereof; and
    surgically manipulating a tissue of the patient based, at least in part, on optical detection of the agent's fluorescence in the ureter and distinguishing the ureter from the surrounding tissue during the abdominal surgery.

3. A process for using a fluorescent agent in a surgical procedure, the process comprising:
    administering a renally excretable fluorescent agent into the bloodstream of a patient, wherein the renally excretable optical agent is selected from the group consisting of phenylxanthenes, phenothiazines, phenoselenazines, cyanines, indocyanines, squaraines, dipyrrolo pyrimidónes, anthraquinones, tetracenes, quinolines, pyrazines, acridines, acridones, phenanthridines, azo dyes, rhodamines, phenoxazines, azulenes, azaazulenes, triphenyl methane dyes, indoles, benzoindoles, indocarbocyanines, benzoindocarbocyanines, derivatives having the general structure of 4,4-difluoro-4-bora-3a,4a-diaza-s-indacene, and conjugates thereof and derivatives thereof;

irradiating a ureter of the patient with infrared radiation, visible radiation, ultraviolet radiation or combinations thereof to excite the agent and cause the agent to fluoresce;

subsequent to the administering, detecting the agent's fluorescence based, at least in part, on the irradiating; and determining if the agent is retained in the urine within the ureter based, at least in part, on the detecting fluorescence.

4. The process of claim 1, wherein the renally excretable optical agent is selected from fluorescein, and 3,6-diaminopyrazine-2,5-dicarboxylic acid.

5. The process of claim 1, wherein the renally excretable optical agent is administered intravenously.

6. The process of claim 1, wherein the agent is detected using at least one of unaided eye, camera, charged coupled device, photomultiplier tube, avalanche diode, and photodiodes.

7. The process of claim 1, wherein the surgical procedure is selected from total or partial hysterectomy, oophorectomy, tubal ligation, surgical removal of ovarian cysts, anterior repair of the vaginal wall, caesarean section, repair of a pelvic prolapse, pelvic mass resection, removal of a fallopian tube, adnexectomy, removal of an ectopic pregnancy, vasectomy, prostatectomy, hernia repair surgery, colectomy, cholecystectomy, appendectomy, hepatobiliary surgery, splenectomy, distal or total pancreatectomy, the Whipple procedure, and abdominal or pelvic lymphadenectomy.

* * * * *